United States Patent [19]

Phillips et al.

[11] Patent Number: 5,306,694
[45] Date of Patent: Apr. 26, 1994

[54] PESTICIDAL 1-(2-PYRIDYL)-PYRAZOLE

[75] Inventors: Jennifer L. Phillips, Apex; Philip R. Timmons, Durham; Gail S. Powell, Raleigh; Michael T. Pilato, Raleigh; David T. Chou, Raleigh; Jamin Huang, Chapel Hill, all of N.C.

[73] Assignee: Rhone-Poulenc Inc., Research Triangle Park, N.C.

[21] Appl. No.: 79,221

[22] Filed: Jun. 17, 1993

Related U.S. Application Data

[63] Continuation of Ser. No. 643,530, Jan. 18, 1991, abandoned.

[51] Int. Cl.$^5$ .................. A01N 43/40; C07D 401/00
[52] U.S. Cl. .................................. 504/253; 546/278; 546/279
[58] Field of Search ................. 546/279, 278; 504/253

[56] References Cited

U.S. PATENT DOCUMENTS

| | | | |
|---|---|---|---|
| 4,622,330 | 11/1986 | Bochis et al. | 546/279 |
| 4,770,692 | 9/1988 | Setter et al. | 71/92 |
| 4,772,312 | 9/1988 | Schallner et al. | 71/92 |
| 4,804,675 | 2/1989 | Jensen-Korte et al. | 514/407 |
| 4,918,085 | 4/1990 | D'Silva et al. | 514/407 |

FOREIGN PATENT DOCUMENTS

| | | |
|---|---|---|
| 249033 | 12/1987 | European Pat. Off. . |
| 284030 | 9/1988 | European Pat. Off. . |
| 295117 | 12/1988 | European Pat. Off. . |
| 63-174905 | 7/1988 | Japan . |
| 63-313773 | 12/1988 | Japan . |
| 2-142785 | 5/1990 | Japan . |
| 87/03781 | 7/1987 | PCT Int'l Appl. . |
| 2136427 | 9/1984 | United Kingdom . |

OTHER PUBLICATIONS

Kahn & Pinto, J. Heterocyclic Chem. 18, 9–14 (1981).

Primary Examiner—C. Warren Ivy
Assistant Examiner—Celia Chang
Attorney, Agent, or Firm—James G. Passé

[57] ABSTRACT

The invention describes novel 1-(2-pyridyl)pyrazoles of formula (I)

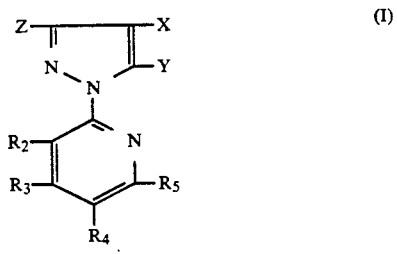

wherein typically preferred substituents are:

X is $S(O)_nR_1$, in which $R_1$ is an alkyl group, preferably a methyl group, which is fully substituted by halogen atoms, and n is 0, 1 and 2;

Y is hydrogen, halogen, cyano, alkylsulfenyl, alkylsulfinyl, alkylsulfonyl, alkoxy, amino, alkylamino, dialkylamino, trialkylammonium salt, cyanoalkylamino, alkoxyalkylamino, alkoxycarbonylamino, alkylcarbonylamino, haloalkylcarbonylamino, alkylaminocarbonylamino, dialkylaminocarbonylamino or alkoxyalkylideneimino, wherein the alkyl and alkoxy moieties are a linear or branched chain, containing one to four carbon atoms, and the halo-substitution consists of one or more halogen atoms, which are the same or different, up to full substitution of the alkyl moiety;

Z is cyano; and $R_2$, $R_3$, $R_4$, and $R_5$ are individually hydrogen, halogen or an unsubstituted or halo-substituted alkyl or alkoxy, cyano or nitro; with the proviso that at least one of $R_2$ to $R_5$ is other than hydrogen.

The invention further describes intermediates and processes to make the compounds, compositions of the compounds, and methods of use of the compounds for the control of arthropods (mites, aphids or insects), nematodes, helminths, or protozoa.

24 Claims, No Drawings

PESTICIDAL 1-(2-PYRIDYL)-PYRAZOLE

This is a continuation of co-pending application Ser. No. 07/643,530, filed on Jan. 18, 1991, now abandoned.

BACKGROUND OF THE INVENTION

1. Field of the Invention

The present invention relates to new 1-(2-pyridyl)-pyrazoles, intermediates thereto, and processes to make the compounds. The invention further pertains to compositions of said compounds and methods, using said compounds, for the control of arthropod, nematode, helminth or protozoan pests. In particular, it pertains to the application of compounds or compositions thereof in agricultural methods of use, particularly as pesticides, for controlling arthropods, especially aphids or foliar or soil insects, without causing injury to crop plants.

2. Description of the Related Art

Various 1-(substituted phenyl or pyridyl)-substituted-pyrazole compounds are known to exhibit a number of different types of pesticidal activity, including activity as herbicides, plant growth regulators, fungicides, bactericides, insecticides, and nematicides. Included among these are the following:

JP 63-313773 discloses as herbicides, bactericides, and fungicides 1-(substituted-2-pyridyl)-5-substitutedaminopyrazoles, which are unsubstituted in the 3-position of the pyrazole ring;

JP 63-174905 discloses as fruit thinning plant growth regulators 1-(substituted-2-pyridyl)-5-substitutedaminopyrazoles, which are unsubstituted or alkyl substituted in the 3-position of the pyrazole ring;

U.S. Pat. No. 4,772,312 discloses as herbicides 1-(substituted-2-pyridyl)-5-substitutedaminopyrazoles, which are unsubstituted or alkyl substituted in the 3-position of the pyrazole ring;

GB 2,136,427 discloses as herbicides 1-(substituted-2-pyridyl)-5-substitutedamino-4-cyanopyrazoles, which are unsubstituted at the 3-position of the pyrazole ring;

Khan and Pinto, J. Heterocyclic Chem., 18, 9-14 (1981) is a chemistry paper which discloses 1-(substituted-2-pyridyl)pyrazoles, which are unsubstituted or substituted by methyl, phenyl or p-nitrophenyl in the 3-position of the pyrazole ring; no biological activity is described;

EP 295,117 and WO 87 03781 disclose for the control of arthropod, nematode, helminth and protozoan pests 1-(substituted phenyl)pyrazoles;

U.S. Pat. No. 4,804,675 discloses as insecticides, acaricides, and nematicides 1-(substituted-2-pyridyl)-5-substitutedaminopyrazoles, which are unsubstituted or alkyl or haloalkyl substituted in the 3-position of the pyrazole ring;

JP 2142-785 discloses as herbicides 1-(substituted-2-pyridyl)-4-chloro-5-substitutedaminopyrazoles, which are unsubstituted in the 3-position of the pyrazole ring;

EP 284,030 discloses as herbicides 1-(substituted-2-pyridyl)-4-nitro-5-substitutedalkoxypyrazoles, which are unsubstituted in the 3-position of the pyrazole ring;

U.S. Pat. No. 4,770,692 discloses as herbicides and plant growth regulators 1-(substituted-2-pyridyl)-4-nitro-(or cyano-) pyrazoles, which are unsubstituted or alkyl or haloalkyl substituted in the 3-position of the pyrazole ring along with a variety of substituents in the 5-position;

EP 249,033 discloses as insecticides, acaricides, and nematicides 1-(substituted-2-pyridyl)pyrazoles which are substituted on the pyrazole ring by hydrogen, alkyl or haloalkyl in the 3-position, alkylthio or oxidized states thereof in the 4-position, and alkoxy or alkylthio in the 5-position; and U.S. Pat. No. 4,918,085 discloses as compounds for the control of arthropod, nematode, helminth and protozoan pests 1-(substituted phenyl)-5-alkoxy-3-cyano-5-sulfenylalkylpyrazoles.

It is thus apparent that the nature and position of substituent groups on a pyrazole ring provide widely different types of biological activity which type and level of activity is not readily apparent.

SUMMARY OF THE INVENTION

The present invention pertains to novel 1-(substituted-2-pyridyl)pyrazole compounds which exhibit unexpected and excellent pesticidal properties, especially as insecticides (especially aphicides) or acaricides (miticides).

The compounds, including their isomers, e.g., diastereo and optical isomers, have the following general formula (I),

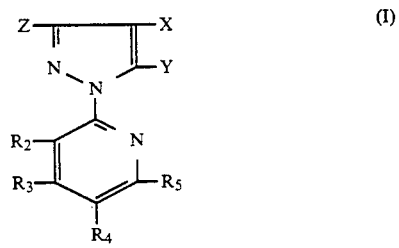

wherein:

X is halogen, nitro, or unsubstituted or halo-substituted alkylsulfenyl, alkylsulfinyl or alkylsulfonyl, wherein the alkyl moiety is a linear or branched chain, containing one to four carbon atoms, and the halo-substitution consists of one or more halogen atoms, which are the same or different, up to full substitution of the alkyl moiety;

Y is hydrogen, halogen, cyano, alkylsulfenyl, alkylsulfinyl, alkylsulfonyl, alkoxy, amino, alkylamino, dialkylamino, trialkylammonium salt, cyanoalkylamino, alkoxyalkylamino, alkoxycarbonylamino, alkylcarbonylamino, haloalkylcarbonylamino, alkylaminocarbonylamino, dialkylaminocarbonylamino or alkoxyalkylideneimino, wherein the alkyl and alkoxy moieties are a linear or branched chain, containing one to four carbon atoms, and the halo-substitution consists of one or more halogen atoms, which are the same or different, up to full substitution of the alkyl moiety;

Z is cyano or halogen; and $R_2$, $R_3$, $R_4$, and $R_5$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that at least one of $R_2$ to $R_5$ is other than hydrogen.

According to a preferred feature of the invention, the pesticidal compounds are selected from amongst the compounds of formula (I), wherein X is S(O)$_n$R$_1$, having a formula (II),

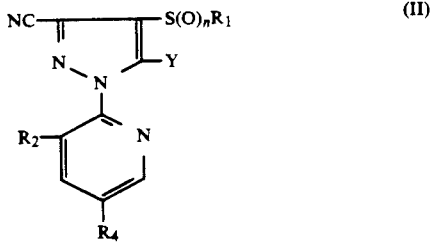

wherein:

Y is hydrogen, halogen, cyano, alkylsulfenyl, alkylsulfinyl, alkylsulfonyl, alkoxy, amino, alkylamino, dialkylamino, trialkylammonium salt, cyanoalkylamino, alkoxyalkylamino, alkoxycarbonylamino, alkylcarbonylamino, haloalkylcarbonylamino, alkylaminocarbonylamino, dialkylaminocarbonylamino or alkoxyalkylideneimino, wherein the alkyl and alkoxy moieties are a linear or branched chain, containing one to four carbon atoms, and the halo-substitution consists of one or more halogen atoms, which are the same or different, up to full substitution of the alkyl moiety;

R$_1$ is a linear or branched alkyl of one to four carbon atoms, which is substituted by one or more halogen atoms, which are the same or different, up to full substitution of the alkyl group;

n is 0, 1 or 2; and

R$_2$ and R$_4$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that one of R$_2$ and R$_4$ is other than hydrogen.

Still further preferred compounds of formula (II) are those compounds having a formula (IIa), wherein:

Y is amino, alkylamino, alkylsulfenyl, alkylsulfinyl, alkylsulfonyl, alkoxyalkylamino, alkylcarbonylamino, haloalkylcarbonylamino or alkoxyalkylideneimino, wherein the alkyl and alkoxy moieties are a linear or branched chain, containing one to four carbon atoms, and the halo-substitution consists of one or more halogen atoms, which are the same or different, up to full substitution of the alkyl moiety;

R$_1$ and n are as defined in formula (II);

R$_2$ is hydrogen or halogen;

R$_4$ is hydrogen, halogen, haloalkyl or haloalkoxy, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that one of R$_2$ and R$_4$ is other than hydrogen.

Even more specifically, preferred compounds of formula (IIa) are those having a formula (IIb), wherein:

Y is amino, alkylamino, alkoxymethylamino or alkoxyalkylideneimino, wherein the alkyl and alkoxy moieties contain one or two carbon atoms;

R$_1$ is trifluoromethyl, dichlorofluoromethyl or chlorodifluoromethyl;

n is 0, 1 or 2;

R$_2$ is bromine, chlorine or fluorine; and

R$_4$ is bromine, chlorine, fluorine, trifluoromethyl or trifluoromethoxy.

The following are some of the representative preferred compounds of formula (II), described subsequently in EXAMPLES 1-27 in the categories identified below:

Good-High aphicidal activity:
Compounds of EXAMPLES 1, 2, 3, 5, 6, 8, 9, 10, 14, 18, 20, 21 and 26;

Good-High aphicidal and broad spectrum insecticidal activity:
Compounds of EXAMPLES 1, 2, 3, 5, 6, 8, 9, 10, 14 and 18;

Good insecticidal activity on grain (rice) hopper pests:
Compounds of EXAMPLES 1, 2, 5, 10 and 18;

Good soil insecticidal activity:
Compounds of EXAMPLES 6, 10, and 18;

Good systemic insecticidal activity on foliar pests (especially insects or aphids) via root uptake:
Compounds of EXAMPLES 2, 3, 9, 10, 14 and 21.

It is an object of the present invention to provide new compounds of the 1-(2-pyridyl)pyrazole family together with processes for their preparation and intermediates thereto.

A second object of the present invention is to provide, for example, agronomically or medicinally acceptable compositions.

A third object of the present invention is to provide highly active compounds for use against: arthropods, especially aphids or insects; plant nematodes; or helminth or protozoan pests. The compounds are thus advantageously used, for example, in agricultural or horticultural crops, forestry, veterinary medicine or livestock husbandry, or in public health.

A forth object of the present invention is to provide compounds with broad spectrum activity as insecticides, miticides, aphicides or nematicides, by either soil or foliar application or seed treatment, including via systemic action.

Still another object of the present invention is to provide compounds which are highly active, especially on sucking insect species (particularly grain pests or aphid species) via systemic action.

These and other objects of the invention shall become readily apparent from the detailed description of the present invention.

DESCRIPTION OF THE PREFERRED EMBODIMENTS

METHODS OR PROCESSES OF SYNTHESIS

The compounds of general formula (I) can be prepared by the application or adaptation of known methods (i.e. methods heretofore used or described in the chemical literature): generally pyrazole ring formation followed wherein necessary by changing substituents. It is to be also understood that, in the description of the following process methods, the sequences for the introduction of the various groups on the pyrazole ring may be performed in a different order and that suitable protecting groups may be required as will be apparent to those skilled in the art. Also compounds of general formula (I) may be converted by known methods into other compounds of general formula (I).

In the following description of process methods when symbols appearing in formulae are not specifically defined, it is to be understood that they are "as herein before defined" in accordance with the first definition of each symbol in this specification. The term "protection" shall include conversion to a suitable non-reactive group which may be reconverted when desired, as well as the addition of groups which render the functionality non-reactive. Within the process definitions, unless otherwise stated, amino refers to the unsubstituted amino group.

The invention embraces particular intermediate compounds, useful to make certain of the herein contemplated compounds. Such preferred intermediate compounds, prepared as described herein, are defined in the following methods. In particular, intermediates that are more preferred have $R_2$ to $R_5$ as defined by formula (I) of the invention or as defined by formula (II), wherein $R_3$ and $R_4$ are each hydrogen or more specifically preferred $R_2$ and $R_4$ definitions therein.

The 1-(2-pyridyl)pyrazoles of the invention can be prepared by a variety of different methods. According to preferred synthetic methods, the compounds of the invention can be obtained from an intermediate 4, by initially cyclizing an alkyl 2-oxo-3-cyanopropionate 2, initially obtained by acid neutralization of its corresponding enolate salt 1, in which M is a metal cation, with an appropriately substituted 2-pyridylhydrazine 3, followed by further substitution or derivatization. The formation of a useful and novel intermediate, 1-(sub-stituted-2-pyridyl)-3-alkoxycarbonyl-5-aminopyrazole 4, wherein R is a $C_{1-4}$ lower alkyl, preferably methyl or ethyl and $R_2$ to $R_5$ are as defined in formula (I) is as shown below.

Starting materials 1 and 3 are either commercially available or may be prepared according to well known literature procedures familiar to one skilled in the art. The aqueous solution of the enolate salt is first acidified with an inorganic acid such as sulfuric acid. The intermediate 2 is then extracted into an organic solvent and then added to a solution of the 2-pyridylhydrazine 3 in a lower ($C_{1-4}$) alkyl alcohol such as methanol or ethanol. After in situ formation of an intermediate hydrazone, a base such as sodium bicarbonate is added to catalyze the cyclization in situ to the 1-(2-pyridyl)-pyrazole 4.

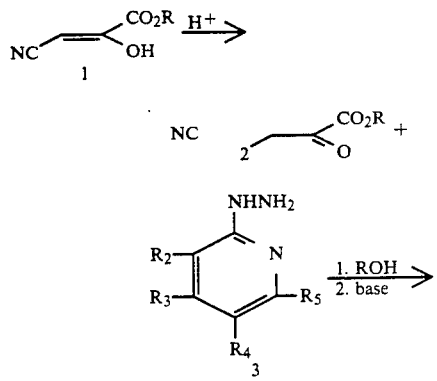

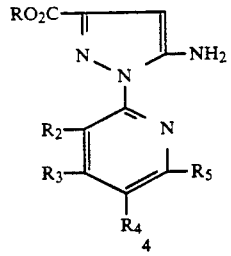

Compounds of formula (I) of the invention are then prepared by reaction of compounds of formula 4 according to the subsequently described Methods introducing the various substituents, particularly X, Y and Z.

Particularly useful and novel intermediate 2-pyridylpyrazole compounds, discussed in the Methods herein for the preparation of compounds of the invention of formula (I), are specifically compounds of formula 4, 9 or 10, corresponding to compounds of an intermediate formula (III), compounds of formula 5, 6, 11 or 13 corresponding to compounds of an intermediate formula (IV), and compounds of a formula (V) defined as follows:

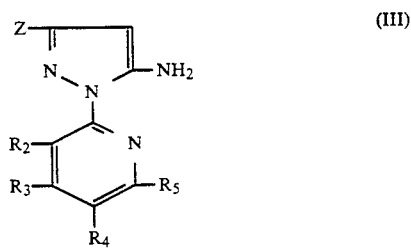

wherein:

Z is $C_{1-4}$ alkoxycarbonyl, aminocarbonyl or cyano; and $R_2$, $R_3$, $R_4$, and $R_5$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that at least one of $R_2$ to $R_5$ is other than hydrogen;

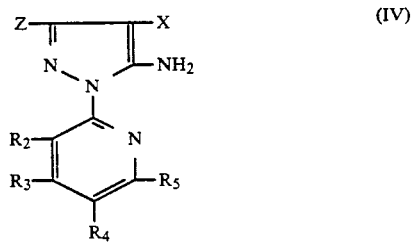

Z is $C_{1-4}$ alkoxycarbonyl or aminocarbonyl;

X is halogen, nitro, or unsubstituted or halo-substituted alkylsulfenyl, alkylsulfinyl or alkylsulfonyl, wherein the alkyl moiety is a linear or branched chain, containing one to four carbon atoms, and the halo-substitution consists of one or more halogen atoms, which are the same or different, up to full substitution of the alkyl moiety;

$R_2$, $R_3$, $R_4$, and $R_5$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that at least one of $R_2$ to $R_5$ is other than hydrogen; and

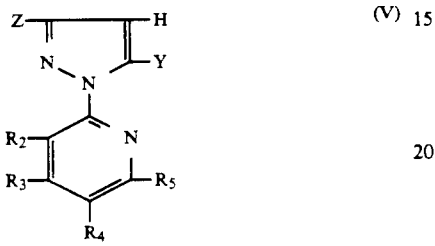

(V)

wherein, Y, Z, $R_2$, $R_3$, $R_4$ and $R_5$ are as defined in formula (I).

In particular, the more preferred 4-sulfenated 1-(substituted-2-pyridyl)pyrazoles ($X=S(O)_nR_1$, wherein n and $R_1$ are previously defined) compounds of formula (I) of this invention can be prepared by a variety of methods. Two preferred methods are illustrated by reaction Paths A and B in SCHEME I.

SCHEME I(PATH A)

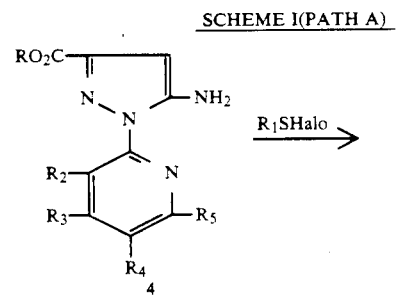

$\xrightarrow{R_1SHalo}$

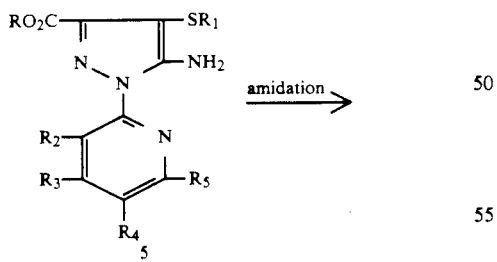

$\xrightarrow{amidation}$

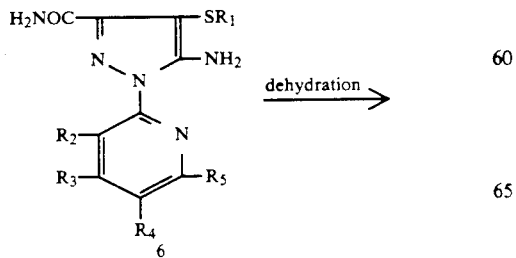

$\xrightarrow{dehydration}$

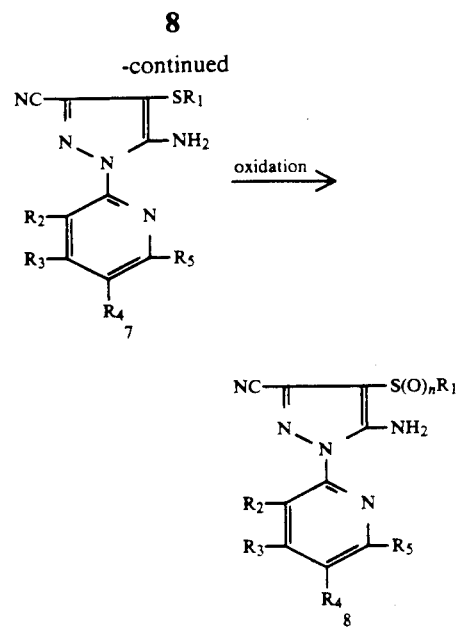

$\xrightarrow{oxidation}$

SCHEME I(PATH B)

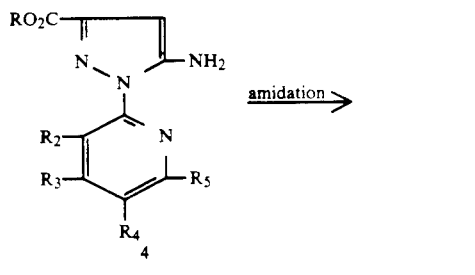

$\xrightarrow{amidation}$

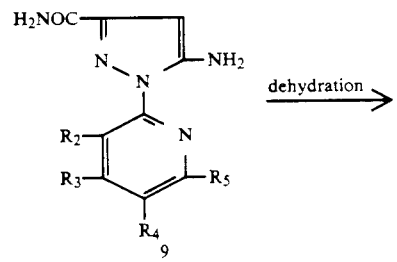

$\xrightarrow{dehydration}$

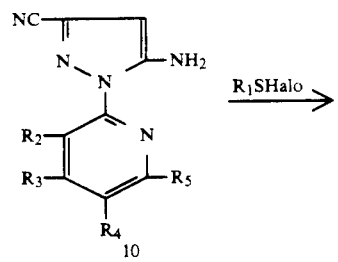

$\xrightarrow{R_1SHalo}$

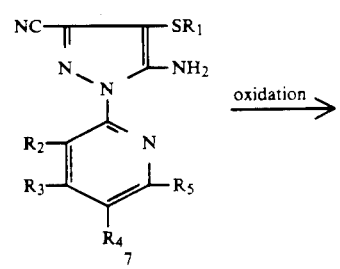

$\xrightarrow{oxidation}$

-continued

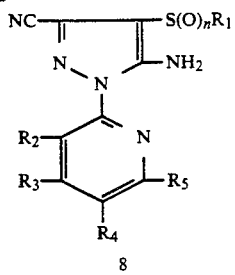

8

Method I

A compound of general formula (I), further of a formula (Ia) subsequently defined and more specifically of a formula 7 or 8, in which X is alkylsulfenyl, haloalkylsulfenyl, alkylsulfinyl, haloalkylsulfinyl, alkylsulfonyl or haloalkylsulfonyl, Y is amino, Z is cyano and $R_2$, $R_3$, $R_4$ and $R_5$ are as defined in general formula (I), is prepared from the intermediate compound of formula 4, in which X is hydrogen, Y is amino, Z is alkoxycarbonyl and $R_2$ to $R_5$ are as defined, by procedures described in SCHEME I, Paths A and B as follows:

a) In SCHEME I, Path A, the 3-alkoxycarbonyl-5-aminopyrazole intermediate 4 is reacted with an alkyl or haloalkylsulfenyl halide, $R_1$SHalo, in which $R_1$ is alkyl or haloalkyl as previously defined and Halo is preferably chlorine, to give an intermediate compound of formula 5, in which Y is $SR_1$. The reaction is conveniently conducted in an inert aprotic organic solvent such as a chlorinated hydrocarbon, a hydrocarbon, an ether, etc., preferably in dichloromethane, optionally with an acid acceptor such as pyridine, a tertiary amine or an alkali metal carbonate. The reaction is carried out between about $-25°$ C. and about 100° C. depending on the boiling point of the sulfenyl halide reagent and the solvent. Alternatively, the sulfenylation is conducted in an organic acid such as glacial acetic acid, between about 5° C. and about 100° C.

The intermediate carboxamide 6 is prepared from the intermediate ester 5 by reaction with ammonia in an inert organic solvent, in the presence of a Lewis acid catalyst such as trimethylaluminum, at a temperature between about $-78°$ C. and about 50° C. Alternatively, the intermediate ester 5 is hydrolyzed to the corresponding acid and then converted to the acid chloride by well known chemistry. This is then further reacted with ammonia to afford the intermediate carboxamide 6.

The intermediate carboxamide 6 is then dehydrated to the nitrile 7 using standard dehydrating agents, such as phosphorous oxychloride or phosphorous pentoxide, optionally in an inert organic solvent, and usually at reflux temperature of the solvent which is typically between about 30° C. and about 180° C.

The oxidation of the sulfide 7 to obtain 8, the sulfoxide, n=1, or the sulfone, n=2, is carried out using, for example, an appropriate quantity of peracetic acid, trifluoroperacetic acid, m-chloroperbenzoic acid, hydrogen peroxide, a combination of peracetic acid and hydrogen peroxide, or potassium peroxymonosulfate which is commercially available as Oxone ®. The reaction is usually conducted in an inert organic solvent typically between about $-30°$ C. and about 180° C.

b) In an alternative path, SCHEME I, Path B, the intermediate ester 4 is first converted to the intermediate carboxamide 9 by reaction of the intermediate ester 4 with a base such as ammonium hydroxide in an alkyl alcohol at ambient temperature. The resulting intermediate carboxamide 9 is then dehydrated to the intermediate nitrile 10 in a similar manner as described for 6 to 7 in Path A. Optionally, the dehydration of 9 to 10 is conducted using an anhydride such as trifluoroacetic anhydride and an organic base such as pyridine in an inert organic solvent such as dioxane or tetrahydrofuran at a temperature between about $-30°$ C. and about 100° C.

The sulfenylation of the nitrile 10 to 7 is conducted in a manner similar to that described for compound 4 to 5 in Path A. The sulfenyl compound 7 is then oxidized to 8 as described above.

Method II

A compound of general formula (I), further of a formula (Ia) subsequently defined and more specifically of a formula 13, in which X is halogen or nitro, Y is amino (or protected amino), Z is cyano, R is a $C_{1-4}$ lower alkyl, and $R_2$, $R_3$, $R_4$ and $R_5$ are as defined in formula (I), is prepared by direct halogenation or nitration of an intermediate compound of formula 4 as defined above, followed by amidation and dehydration according to the following procedures:

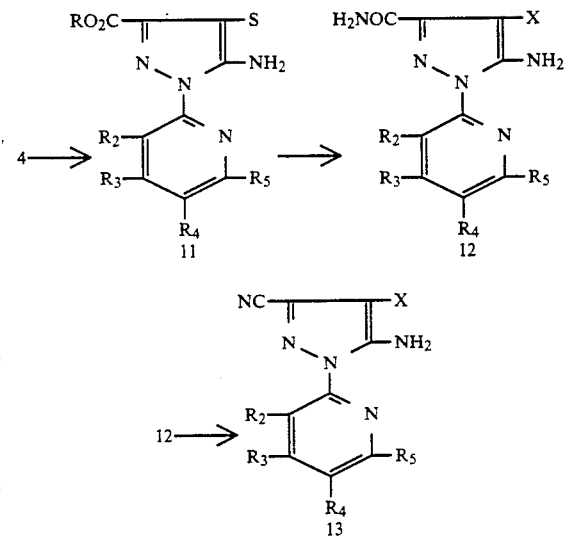

a) An intermediate compound of formula 11, in which X is halogen, is first obtained by reacting the intermediate compound of formula 4, in which X is hydrogen, with a halogenating agent such as sulfuryl chloride, thionyl chloride, an N-halosuccinimide, chlorine or bromine and optionally with an acid acceptor or a catalyst such as a Lewis acid. The reaction is conducted in an inert aprotic organic solvent such as a chlorinated hydrocarbon, an ether or acetonitrile. The reaction is carried out between about $-50°$ C. and about 150° C., preferably between about $-10°$ C. and about 110° C., depending on the reactivity of the pyrazole and the reactivity of the halogenating agent used;

b) An intermediate compound of formula 11, in which X is nitro, is first obtained by reacting the intermediate compound of formula 4, in which X is hydrogen, with a nitrating agent, such as a mixture of concentrated nitric acid and sulfuric acid in acetic acid or acetic anhydride, dinitrogen pentoxide in a halogenated alkane, an ester of nitric acid such as ethyl nitrate, a mixed anhydride such as acetyl nitrate or nitryl halide, optionally with a Friedel-Crafts catalyst such as ferric chloride or methyl nitrate, or a nitronium salt such as nitronium tetrafluoroborate. The reaction is conducted in a suitable solvent, such as acetic acid, acetic anhydride, tetramethylene sulfone, tetrahydrofuran or water under neutral, basic or acidic conditions at a reaction temperature from about −50° C. to about 155° C. A preferred procedure is to conduct the nitration using nitryl chloride in the presence of titanium tetrachloride in tetramethylene sulfone at a reaction temperature between about −10° C. and about 25° C.;

c) An intermediate compound of formula 11, in which X is halogen or nitro, is converted to an intermediate compound of formula 12 by amidation of the alkoxycarbonyl group to a carboxamide group according to procedures described in conversion of 5 to 6 in Method Ia; and d) A compound of formula 13, i.e. of formula (Ia), in which X is halogen or nitro is then prepared by dehydration of the intermediate compound of formula 12 according to the procedures described for conversion of 6 to 7 in Method Ia.

Method III

A compound of general formula (I), further of a formula (Ia) subsequently defined and more specifically of a formula 16 or 16a, in which Z is halogen, Y is amino (or protected amino), R is $C_{1-4}$ lower alkyl, and X, $R_2$, $R_3$, $R_4$ and $R_5$ are as defined in general formula (I), is prepared from an intermediate compound of formula 5 from Method Ia, in which Z is alkoxycarbonyl, X is alkylsulfenyl or haloalkylsulfenyl, and Y is amino or from an intermediate compound of formula 11 from Method IIa, in which X is halogen or nitro, Z is alkoxycarbonyl, and Y is amino, according to the following procedures:

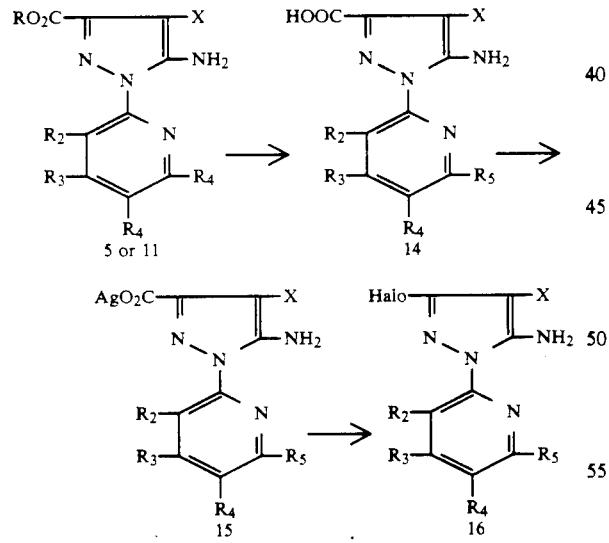

a) The intermediate compound of formula 5 or 11, in which Z is alkoxycarbonyl (i.e., an ester), is hydrolyzed under acid or base catalysis, according to well known literature procedures, to give an intermediate compound of formula 14, in which Z is carboxy; and b) The intermediate compound of formula 14, in which Y is amino (or optionally protected amino), is first converted to an intermediate dry silver salt compound of a formula 15, which is then reacted to give the compound of formula 16, i.e., of formula (Ia), in which X is halogen, according to the Hunsdiecker reaction. The reaction is conducted with a halogen, especially bromine, in an inert organic solvent such as carbon tetrachloride, generally at reflux temperature of the solvent, the reaction temperature being between about 50° C. and about 200° C.; or c) Optionally the compound of formula 16, in which X is alkylsulfenyl or haloalkylsulfenyl, (sulfide, n=0) is oxidized to the corresponding sulfinyl (sulfoxide, n=1) or sulfonyl (sulfone, n=2) analog of formula 16a by the oxidation methods described for conversion of 7 to 8 in Method Ia.

Method IV

A compound of general formula (I), further of a formula 17 or (Ib), in which an amino derivative Y is alkylamino, dialkylamino, trialkylammonium salt, cyanoalkylamino, alkoxyalkylamino, alkoxycarbonylamino, alkylcarbonylamino, haloalkylcarbonylamino, alkylaminocarbonylamino, dialkylaminocarbonylamino or alkoxyalkylideneimino, and X, Z, $R_2$, $R_3$, $R_4$ and $R_5$ are as defined in general formula (I), is prepared by appropriate derivatization of a compound of a formula (Ia) corresponding to compounds of a formula 7, 8, 13, 16 or 16a, in which Y is amino, and in which the other substituents are as defined.

In general, derivatization of the compound of formula (Ia), in which Y is amino, is accomplished by alkylating, for example with an appropriate substituted alkylhalide (e.g., in which the halide is Cl, Br or I) or an appropriate substituted acylhalide (e.g., acylchloride), in an inert organic solvent, optionally in the presence of a base as an acid acceptor or in the presence of a catalyst. The reactions are conducted according to standard literature procedures usually at a temperature between about 0° C. and about 100° C., depending upon the nature of the solvent and the alkylating or acylating agent used. Typical procedures are as follows:

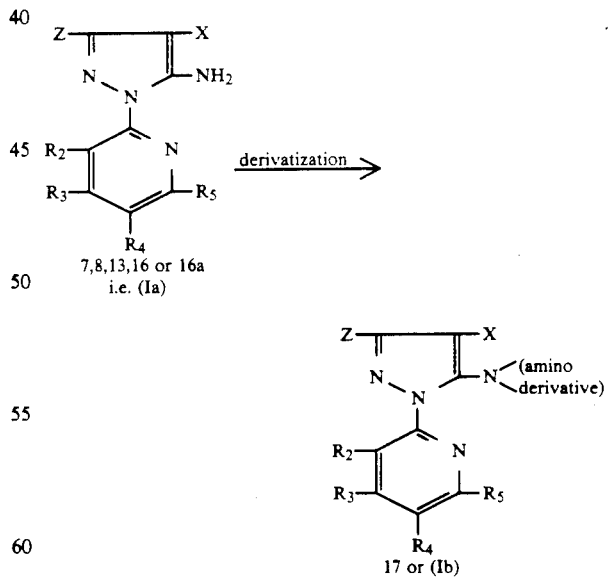

a) The compound of formula 17 or (Ib), wherein the amino derivative Y is alkylamino, dialkylamino, trialkylammonium salt, cyanoalkylamino or alkoxyalkylamino, is conveniently prepared by monoalkylation, dialkylation and trialkylation using an appropriate unsubstituted or substituted alkylating agent such as an alkyl iodide or dialkyl sulfate, in an inert solvent such as acetonitrile, tetrahydrofuran or dimethoxyethane, at a reaction temperature between about 0° C. and about 160° C., optionally in the presence of a base such as potassium carbonate or triethylamine. Alternatively, for methylation, an Eschweiler-Clark Reaction is utilized to achieve the desired N-methylation. This reductive methylation can be conveniently conducted by reacting an amine of formula (Ia), i.e. of formula 7, 8, 13, 16 or 16a with formaldehyde and formic acid. The procedure is similar to that reported by Clark et. al. J. Am. Chem. Soc., 55, 4571, 1933;

b) The compound of formula 17 or (Ib), in which the amino derivative Y is alkylcarbonylamino or haloalkylcarbonylamino, is conveniently prepared from a compound of formula (Ia), i.e., of formula 7, 8, 13, 16 or 16a, in which Y is amino, by a reaction with an appropriate alkyl- or haloalkylcarbonyl halide, such as acetyl chloride or chloroacetyl chloride, in a suitable organic solvent, such as dichloromethane, ethyl ether or tetrahydrofuran, optionally in the presence of an acid acceptor such as pyridine or triethylamine, at a reaction temperature between about −10° C. and about 100° C., preferably between about −10° C. and about 50° C.;

c) The compound of formula 17 or (Ib), in which the amino derivative Y is alkoxycarbonylamino, alkylaminocarbonylamino or dialkylaminocarbonylamino, is conveniently prepared by a two step sequence involving a first step of converting a compound of formula (Ia), i.e. of formula 7, 8, 13, 16 or 16a, in which Y is amino, into its corresponding chlorocarbonylamino or isocyanate intermediate by a treatment with phosgene. The reaction is carried out in an inert organic solvent such as toluene, dichloromethane or tetrahydrofuran at a reaction temperature between about −15° C. and about 100° C., preferably between about −15° C. and about 50° C. In a second step, the chlorocarbonylamino or isocyanate intermediate compound is reacted with an appropriate alkyl alcohol, alkylamine or dialkylamine. The reaction is carried out in an inert organic solvent such as a halogenated alkane, toluene, ether or tetrahydrofuran at a reaction temperature between about −20° C. and about 100° C., preferably between about 0° C. and about 50° C., optionally in the presence of a base such as an amine; or d) A compound of formula 17 or (Ib), in which the amino derivative Y is alkoxyalkylideneimino, is prepared by reacting a compound of formula (Ia), i.e. of formula 7, 8, 13, 16 or 16a, in which Y is amino, with an appropriate alkyl orthoformate. The catalyst used is generally an inorganic acid such as hydrochloric acid or an organic acid such as p-toluenesulfonic acid. The reaction is carried out at a temperature between about −20° C. and about 180° C., preferably between about 0° C. and about 120° C., in the presence of an inert organic solvent such as a hydrocarbon, a chlorinated hydrocarbon, an aromatic, an ether, an alcohol or the like; or the alkyl orthoformate itself may be used as the solvent.

Method V

A compound of formula (I), further of a formula (Ic) and more specifically of a formula 18, in which $Y_{sub}$ is hydrogen, halogen, cyano, alkylsulfenyl, alkylsulfinyl or alkylsulfonyl, and X, Z, $R_2$, $R_3$, $R_4$ and $R_5$ are as defined in general formula (I), is prepared by deamination or substitutive deamination of the compound of formula (Ia), i.e. of formula 7, 8, 13, 16 or 16a, in which the substituents are as defined. The procedures are as follows:

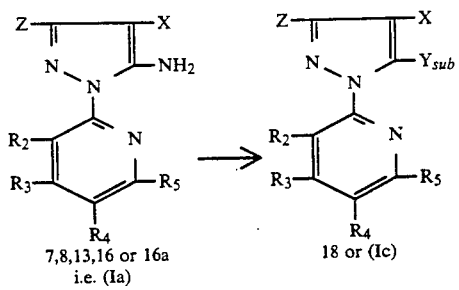

7,8,13,16 or 16a
i.e. (Ia)

18 or (Ic)

a) The desaminopyrazole compound of formula 18, in which $Y_{sub}$ is hydrogen, is prepared by reacting the aminopyrazole compound of formula (Ia), i.e. of formula 7, 8, 13, 16 or 16a, in which Y is amino, with an organic alkylnitrite, such as t-butyl nitrite, or optionally with nitrous acid, in an inert organic solvent such as tetrahydrofuran between about −20° C. and about 180° C., preferably between about 10° C. and about 100° C.; or b) The compound of formula 18, in which $Y_{sub}$ is halogen, cyano or alkylsulfenyl, is prepared initially by deaminating the compound of formula (Ia), i.e. of formula 7, 8, 13, 16 or 16a, as described in Method Va above and then it is immediately reacted by quenching with an agent such as bromoform, cupric chloride, cupric cyanide or dimethyl disulfide. The reaction is usually conducted in an inert organic solvent such as anhydrous acetonitrile, typically at a temperature between about −20° C. and about 180° C., preferably between about 10° C. and about 100° C. A further compound wherein $Y_{sub}$ is alkylsulfinyl or alkylsulfonyl (that is an alkylsulfoxide, in which n=1, or an alkylsulfone, in which n=2, respectively) is then prepared by an oxidation reaction conducted in a similar manner described for the conversion of 7 to 8 as described in Method Ia.

Method VI

A compound of formula (I), further of a formula 18 or (Ic), in which $Y_{sub}$ is alkoxy and X, Z, $R_2$, $R_3$, $R_4$ and $R_5$ are as defined in general formula (I), is prepared from the compound of formula 18, in which $Y_{sub}$ is halogen, prepared in Method Vb. The procedures are as described below:

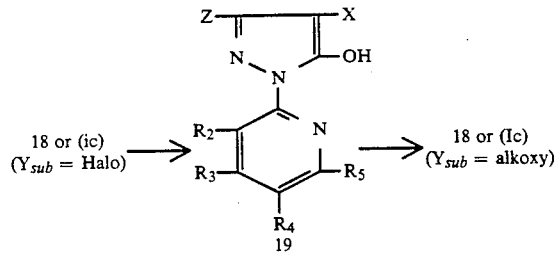

18 or (ic)
($Y_{sub}$ = Halo)

19

18 or (Ic)
($Y_{sub}$ = alkoxy)

a) The intermediate hydroxy compound of formula 19 is prepared by converting the compound of formula 18, in which $Y_{sub}$ is halogen, into the corresponding Grignard reagent or the corresponding lithium derivative following commonly known procedures, then followed by treatment with oxodiperoxymolybdenum(-pyridine)(hexamethylphosphoric triamide) (MoOPH) by a procedure similar to that described by N. J. Lewis et. al. in J. Org. Chem., 42, 1479, (1977). Alternatively, the Grignard reagent or the lithium derivative described above is reacted with a trialkyl borate followed by oxidation with hydrogen peroxide or another oxidizing agent to produce the hydroxy analog by a procedure similar to that reported by M. F. Hawthorne, *J. Org. Chem.*, 22, 1001, (1957), or R. W. Hoffmann and K. Ditrich, Synthesis, (1983), 107; and b) The compound formula 18 or (Ic), in which Y is alkoxy, is prepared from the intermediate hydroxy compound of formula 19, by various standard alkylating methods, such as with an alkylhalide or dialkylsulfate in an inert solvent at a temperature between about $-20°$ C. and about 200° C.

Method VII

A compound of formula (I), further of a formula (Id) subsequently defined and more specifically of a formula 24 or 24a or 26 or 26a, wherein X, which is $S(O)_nR_1$ in which n and $R_1$ are as defined, is alkylsulfenyl, haloalkylsulfenyl, alkylsulfinyl, haloalkylsulfinyl, alkylsulfonyl or haloalkylsulfonyl and Y, Z, $R_2$, $R_3$, $R_4$ and $R_5$ have the meanings of the definition of general formula (I), is alternatively prepared by the following procedures starting from an intermediate compound of formula (V), in which Y, Z, $R_2$, $R_3$, $R_4$ and $R_5$ are as defined in general formula (I), to give an intermediate 21, wherein X is chlorosulfonyl, or an intermediate 25, wherein X is thiocyano. Either of these intermediates is converted to a corresponding disulfide intermediate 22, which is then converted to a sulfenyl compound, 24 or 26, in which X is $SR_1$ and in which $R_1$ is as defined, which in turn may be oxidized to the corresponding sulfoxide or sulfone compound 24a or 26a, X is $S(O)_nR_1$, in which n is 1 or 2. The procedures are as follows:

a) An intermediate of a formula 21, in which X is chlorosulfonyl, and Y, Z, $R_2$, $R_3$, $R_4$ and $R_5$ have the meanings defined in the definition of formula (I), is prepared from an intermediate compound of formula (V), prepared from a compound of formula 4 by a combination of procedures to introduce Y and Z substituents according to Methods Ib, III a-b, IV a-d, V a-b, and VI a-b, in which Y, Z, $R_2$, $R_3$, $R_4$ and $R_5$ are defined herein above, by treatment with chlorosulfonic or dichlorosulfonic acid. The reaction is carried out in the presence of an organic solvent such as methylene chloride, chloroform, carbon tetrachloride or dimethylformamide or using chlorosulfonic acid as solvent at a reaction temperature between about $-10°$ C. and about 160° C. A representative procedure for chlorosulfonation of an aromatic compound is reported in J. March, "Advanced Organic Chemistry", McGraw-Hill publ. (1968), p. 402;

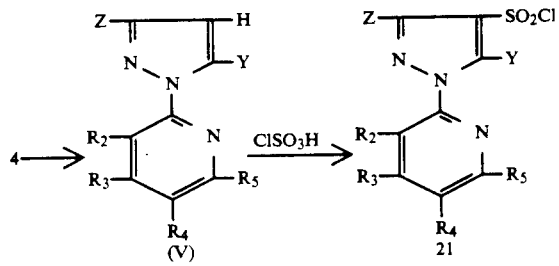

b) An intermediate disulfide compound of the formula 22, in which X is a disulfide moiety and the definitions of Y, Z, $R_2$, $R_3$, $R_4$ and $R_5$ are those given for the definition of formula (I), is prepared from the compound of the formula 21 by treatment with a reducing agent, such as triphenylphosphine, in the presence of an organic solvent, such as tetrahydrofuran, dichloromethane or toluene at a reaction temperature between about $-10°$ C. and about 120° C. A representative example of a procedure for the reduction to p-tolyldisulfide is reported in *J. Org. Chem.* 45, 4792, (1980). Alternatively, disulfenylation is effected using a metal carbonyl such as hexacarbonylmolybdenum in anhydrous tetramethylurea. The procedure of this reaction is reported by H. Alper, *Angew. Chem. Internat.* Edit, 8, 677, (1969). The reaction of the present invention is as follows:

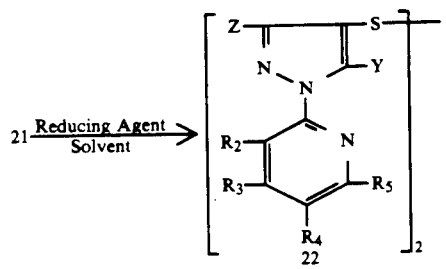

c) A compound of the formula (I), namely of formula 24, wherein the definition of Y, Z, $R_2$, $R_3$, $R_4$ and $R_5$ are those given for the definition of formula (I), and X is haloalkylsulfenyl, preferably perhaloalkylsulfenyl, $R_6S$, in which $R_6$ is $CFR_7R_8$ and $R_7$ and $R_8$ are F, Cl, Br or a perfluoroalkyl group, is prepared by the reaction of a compound of the formula 22 and a perhaloalkane compound of a formula 23, Halo-$CFR_7R_8$, wherein Halo is Cl, Br or I, $R_7$ is F, Cl or Br, and $R_8$ is F, Cl, Br or a perfluoroalkyl group, with a reducing agent which can promote the formation of the free radical $R_6$, $CFR_7R_8$ (from 23, Halo-$CFR_7R_8$). The reducing agent is preferably chosen from a metal consisting of zinc, aluminum, cadmium, manganese or a compound with an oxide of sulfur, e.g., a dithionite or a hydroxymethylsulfinate. The alkaline dithionite, alkaline earth or the metal dithionite corresponds to a formula $M_m(S_2O_4)$, in which m can be 1 or 2 depending upon the valence of the metal M. When a dithionite or a hydroxymethylsulfinate is used, a base is needed. The base, for example, is an alkali metal hydroxide, alkaline earth metal hydroxide, ammonia, alkylamine, triethylbenzylammonium or the salt of a weak acid such as disodium phosphate, sodium metabisulfite, sodium hydrogen sulfite or sodium borate. The solvents used for the reaction are those which can solubilize the dithionite or the hydroxymethylsulfinate, and the compounds 22 and 23. Useful solvents are acetonitrile, dimethylformamide, formamide, dimethylacetamide, hexamethylphos-phoramide, N-methylpyrrolidone, dimethylsulfoxide or sulfolane. The reaction temperature is between about 10° C. and about 100° C. Typical procedures are similar to those reported by A. Maggiolo, *J. Am. Chem. Soc.*, (1951), 5815 and by P. W. Feit, *Acta. Chem. Scan.*, 16, 297 (1962). The reaction of the present invention is represented by the following equation:

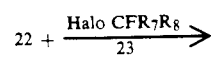

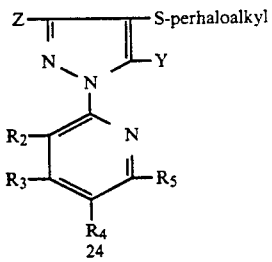

24 d) The intermediate compound, namely of formula 25, in which X is cyanothio and Y, Z, $R_2$, $R_3$, $R_4$ and $R_5$ have the meanings given in the definition of formula (I), is prepared from a compound of formula (V), by treatment with bromine and an alkali metal thiocyanate such as potassium thiocyanate in a suitable solvent such as methanol at a temperature from about −78° C. to about room temperature. The solvent should be inert to and capable of solvolyzing the reactants;

4⟶

(V)⟶

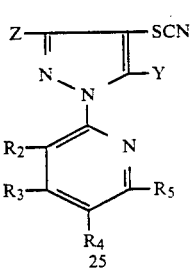

25 e) Alternatively, the compound of formula 24, wherein X is haloalkylsulfenyl, preferably perhaloalkylsulfenyl, is prepared by a sequence of oxidation of the compound of formula 25 to form the intermediate disulfide compound of formula 22, which is then converted into its corresponding haloalkylsulfenyl compound of formula 24. The oxidation is achieved using an oxidizing agent such as hydrogen peroxide in the presence of an alkali metal hydroxide, such as sodium hydroxide, or an amine such as ammonia in a suitable solvent, such as an alcohol, water, tetrahydrofuran, a halogenated alkane or mixed solvent thereof, at a reaction temperature between about −70° C. and about 55° C. Typical procedures are reported by A. Maggiolo, *J. Am. Chem. Soc.*, (1951), 5815 and by P. W. Feit, *Acta. Chem. Scan.*, 16, 297, (1962). The haloalkylsulfenyl compound of formula 24 is prepared by reacting the disulfide intermediate compound of formula 22 with an appropriate perhaloalkane, optionally in the presence of a reducing agent such as a metal consisting of zinc, aluminum, cadmium or manganese;

25⟶

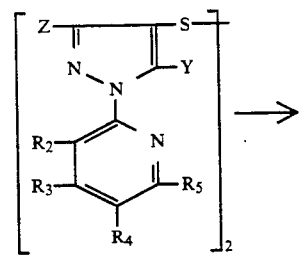

22

24⟶

X = S(O)ₙ perhaloalkyl
(n = 1 or 2)
24a f) A further compound of formula (I), i.e., a compound of formula 26, wherein X is alkylsulfenyl or haloalkylsulfenyl and Y, Z, $R_2$, $R_3$, $R_4$ and $R_5$ are as defined by formula (I), is prepared by treating the compound of formula 25 with an appropriate alkyl halide, $R_1$ Halo, in which $R_1$ is alkyl or haloalkyl as previously defined, preferably an alkyl iodide or an alkyl bromide, in a suitable solvent such as an alcohol, preferably the corresponding alkyl alcohol, in the presence of a base catalyst such as an alkali metal hydroxide or alkali metal carbonate, at a reaction temperature between about −20° C. and about 75° C.; or

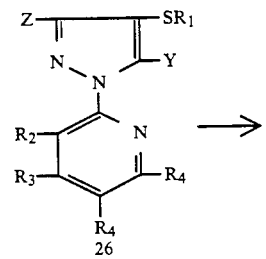

26

X = S(O)ₙ$R_1$
(n = 1 or 2)
26a g) A compound of formula (I), having a formula 24a or 26a, wherein X is alkylsulfinyl, haloalkylsulfinyl, alkylsulfonyl or haloalkylsulfonyl (X=S(O)ₙ$R_1$ in which n is 1 or 2) and Y, Z, $R_2$, $R_3$, $R_4$ and $R_5$ are as defined in formula (I), is prepared from a compound of formulae 24 or 26 by the oxidation procedures described, for example in Method Ia.

Method Generalizations

The above methods or processes of synthesis are not to be construed as limiting and therefore, compounds of the present invention, as well as intermediates and starting materials (particularly the pyridines), can be prepared by application or adaptation of synthesis methods, which are apparent to one skilled in the art, and are commonly known, used or described in the chemical literature. In this regard, it is understood that, for example, the sequence of the synthetic chemical steps may be performed in a different order as appropriate, suitable protecting groups may be employed, and substituent groups may be incorporated when convenient.

In an overall/global manner the foregoing Methods of synthesis may be represented by the following processes of the invention which are described as follows:

P₁. A process of preparation of a compound of formula (I), having a formula (Ia),

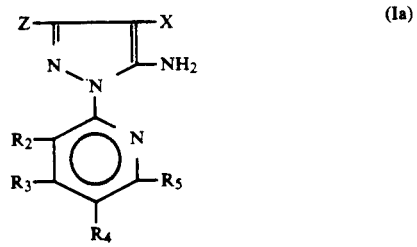

wherein R₂, R₃, R₄ and R₅ are as defined for formula (I), X is alkylsulfenyl, haloalkylsulfenyl, alkylsulfinyl, haloalkylsulfinyl, alkylsulfonyl, haloalkylsulfonyl, halogen or nitro and Z is cyano or halogen, wherein an intermediate ester compound of formula 4,

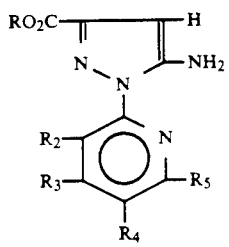

in which R is C₁₋₄ lower alkyl and amino is optionally protected as required:

a) is first reacted with a sulfenyl halide, R₁SHalo in which R₁ is alkyl or haloalkyl, in an organic reaction medium, optionally in the presence of an acid acceptor such as a tertiary amine to obtain an intermediate sulfenylated compound of formula 5, wherein X is alkylsulfenyl or haloalkylsulfenyl, which intermediate compound of formula 5 is then amidated with ammonia in an inert organic solvent, in the presence of a catalyst, at a temperature between about −78° C. and about 50° C. or optionally the intermediate ester 5 is hydrolyzed to the corresponding acid, converted to the acid chloride and then finally is reacted with ammonia to give an intermediate carboxamide compound of formula 6, which then is converted by a dehydrating agent, optionally in an organic solvent, at a temperature between about 30° C. and about 180° C. to a compound of formula (Ia), namely a compound of formula 7, wherein Z is cyano and X is alkylsulfenyl or haloalkylsulfenyl, which compound 7 is then optionally oxidized by known methods such as by a peroxide, to obtain another compound of formula (Ia), namely a compound of formula 8, wherein X is S(O)ₙR₁ in which n is 1 or 2 and R₁ is as defined above, that is to say X is alkylsulfinyl, haloalkylsulfinyl, alkylsulfonyl or haloalkylsulfonyl;

b) is reacted, in a similar manner as described in process P₁a above, first according to the amidation procedure to give an intermediate carboxamide compound of formula 9, which then is converted according to the dehydration procedure to give an intermediate nitrile compound of formula 10, and then is reacted with R₁SHalo according to the sulfenylation procedure to give a compound of formula (Ia), namely a compound of formula 7, which is then optionally oxidized to give a compound of formula (Ia), namely a compound of formula 8;

c) is first halogenated or nitrated according to known procedures to give an intermediate ester compound of formula 11, wherein X is halogen or nitro, which is then reacted, in a similar manner as described in process P₁a above, first according to the amidation procedure to give an intermediate carboxamide compound of formula 12, which is then converted according to the dehydration procedure to give a compound of formula (Ia), namely a compound of formula 13, wherein Z is cyano and X is halogen or nitro; or d) is first converted to the intermediate sulfenylated ester compound of formula 5, according to process P₁a above, or to the halogenated or nitrated intermediate ester compound of formula 11, according to process P₁c above, which compound of formula 5 or 11 is then hydrolyzed by known procedures to an intermediate compound of formula 14, wherein Z is carboxy, which is then converted to an intermediate dry silver salt compound of formula 15, which is then reacted with a halogen, according to a Hunsdiecker procedure, to give a compound of formula (Ia), namely a compound of formula 16, wherein Z is halogen, X is alkylsulfinyl, haloalkylsulfinyl, halogen or nitro, and Y is amino, and optionally the compound of formula 16, wherein X is a alkylsulfenyl or haloalkylsulfenyl is oxidized, according to the procedure described in process P₁a above, to give a compound of formula (Ia), namely a compound of formula 16a, wherein Z is halogen, X is alkylsulfinyl, haloalkylsulfinyl, alkylsulfonyl or haloalkylsulfonyl, and Y is amino.

P₂. A process of preparation of a compound of formula (I) having a formula (Ib).

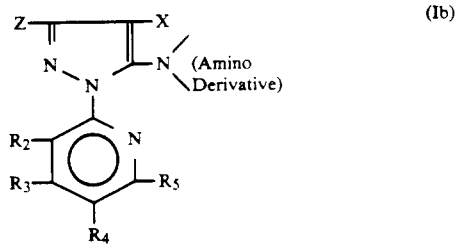

wherein X, Z, R₂, R₃, R₄ and R₅ are as defined for general formula (I) and an amino derivative Y is alkylamino, dialkylamino, trialkylammonium salt, cyanoalkylamino, alkoxyalkylamino, alkylcarbonylamino, haloalkylcarbonylamino, alkoxycarbonylamino, alkylaminocarbonylamino, dialkylaminocarbonylamino or alkoxyalkylideneimino, wherein a compound of formula (Ia),

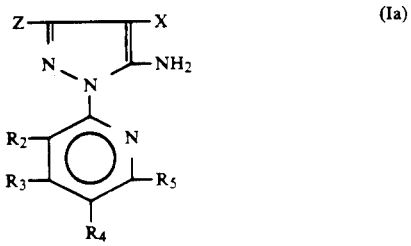

in which X, Z, R₂, R₃, R₄ and R₅ are as defined above, prepared via procedures described in processes P₁a–P₁d:

a) is reacted with an unsubstituted (or cyano or alkoxy substituted) alkylating agent, such as an alkyl iodide or dialkyl sulfate in an inert solvent at a temperature between about 0° C. and 160° C., optionally in the presence of a base or optionally by known Eschweiler-Clark reductive methylation using formaldehyde and formic acid to give a compound of formula (Ib), in which the amino derivative Y is alkylamino, dialkylamino, trialkylammonium salt, cyanoalkylamino or alkoxyalkylamino;

b) is reacted with an alkylcarbonyl halide or haloalkylcarbonyl halide, in an organic solvent at a temperature between about $-10°$ C. and 100° C., optionally in the presence of an acid acceptor, to give a compound of formula (Ib), in which the amino derivative Y is alkylcarbonylamino or haloalkylcarbonylamino;

c) is first reacted with phosgene to give an intermediate chlorocarbonylamino or isocyanato compound, which then is reacted with an alkyl alcohol, alkylamine or dialkylamine in an organic solvent at a temperature between about $-20°$ C. and about 100° C., optionally in the presence of a base, to give a compound of formula (Ib), in which the amino derivative Y is alkoxycarbonylamino, alkylaminocarbonylamino or dialkylaminocarbonylamino; or d) is reacted with an alkyl orthoformate in the presence of a catalyst at a temperature between about $-20°$ C. and about 180° C., optionally in an organic solvent, to give a compound of formula (Ib), in which the amino derivative Y is alkoxyalkylideneimino, particularly alkoxymethylideneimino.

P₃. A process of preparation of a compound of formula (I), having a formula (Ic),

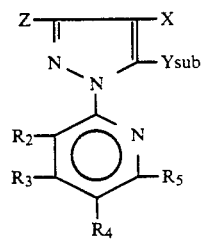

wherein X, Z, $R_2$, $R_3$, $R_4$ and $R_5$ are as defined for general formula (I) and $Y_{sub}$ is hydrogen, halogen, cyano, alkylsulfenyl, alkylsulfinyl, alkylsulfonyl or alkoxy, wherein a compound of formula (Ia),

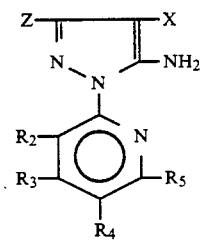

in which X, Z, $R_2$, $R_3$, $R_4$ and $R_5$ are as defined above, prepared via procedures described in processes $P_{1a}$–$P_{1d}$:

a) is deaminated by known procedures, such as with an alkylnitrite, or optionally with nitrous acid, in an inert organic solvent at a temperature between about $-20°$ C. and about 180° C., to convert the compound of formula (Ia), in which Y is amino, into its corresponding diazonium salt, followed by quenching the diazonium salt, at a temperature between about $-20°$ C. and about 180° C., with a quenching agent, according to known procedures, to obtain a compound of formula (Ic), in which $Y_{sub}$ is hydrogen, halogen, cyano or alkylsulfenyl, and then the compound, in which $Y_{sub}$ is alkylsulfenyl is optionally oxidized, according to the procedure of process $P_{1a}$, to a compound of formula (Ic), in which $Y_{sub}$ is alkylsulfinyl or alkylsulfonyl; or b) is first reacted by substitutive deamination, as described above in process $P_{3a}$, to give the compound of formula (Ic), in which $Y_{sub}$ is halogen, which compound is then converted to an organomagnesium or organolithium derivative, then said organometallic derivative is reacted with oxodiperoxymolybdenum(pyridine)(hexamethylphosphoric triamide) or a trialkyl borate and an oxidizing agent such as hydrogen peroxide to obtain an intermediate hydroxy compound of formula 19, which is then finally reacted with an alkylating agent by known alkylating procedures, in an inert solvent at a temperature between about $-20°$ C. and about 200° C., to obtain a compound of formula (Ic) in which $Y_{sub}$ is alkoxy.

P₄. A process of preparation of a compound of formula (I), having a formula (Id),

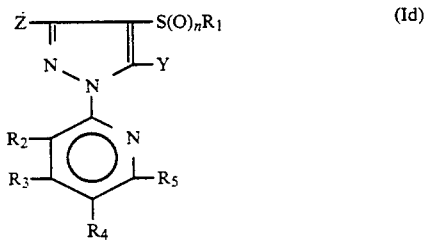

wherein Y, Z, n, $R_1$, $R_2$, $R_3$, $R_4$ and $R_5$ are as defined for general formula (I) and X, which is $S(O)_nR_1$, is alkylsulfenyl, haloalkylsulfenyl, alkylsulfinyl, haloalkylsulfinyl, alkylsulfonyl or haloalkylsulfonyl, wherein an intermediate compound of formula (V),

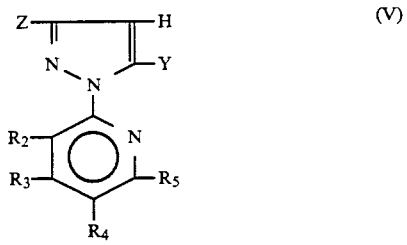

prepared from an intermediate compound of formula 4 of process $P_1$ by a combination of procedures to introduce Y and Z substituents according to one or more of processes $P_{1b}$, $P_2$ a–d, and $P_3$ a–b, in which Y, Z, $R_2$, $R_3$, $R_4$ and $R_5$ are as defined above and Y and Z are optionally protected as required:

a) is first reacted with a mixture of bromine and a metal thiocyanate to give an intermediate compound of formula 25, in which X is thiocyano, which then is treated with an alkylating agent, optionally in the presence of a base to directly give a compound of formula 26, i.e. of formula (Id), in which X is alkylsulfenyl or haloalkylsulfenyl, or optionally the intermediate compound 25, in which X is thiocyano, is first oxidized to a corresponding intermediate disulfide compound, 22, which is then reacted with a perhaloalkane, optionally in the presence of a reducing agent, to give a compound of formula 24; i.e. of formula (Id), in which X is haloalkylsulfenyl, particularly perhaloalkylsulfenyl, then finally the compound 24 or 26, in which X is alkylsulfenyl or haloalkylsulfenyl, is optionally oxidized by known methods similar to those of process $P_{1a}$ to give a compound of formula 24a or 26a, i.e. of formula (Id), in which X is alkylsulfinyl, haloalkylsulfinyl, alkylsulfonyl or haloalkylsulfonyl; or b) is first reacted with chlorosulfonic or dichlorosulfonic acid to give an intermediate compound of formula 21, in which X is chlorosulfonyl, then the chlorosulfonyl compound, 21, is reacted with a reducing agent such as triphenylphosphine to give the same disulfide intermediate 22, described above in process $P_{4a}$, then finally the disulfide 22 is converted by the procedures described above in process $P_{4a}$ to give a compound of formula 24, i.e. of formula (Id), in which X is haloalkylsulfenyl, particularly perhaloalkylsulfenyl or optionally the sulfenyl compound 24 is oxidized to give a compound of formula 24a, i.e. of formula (Id), in which X is haloalkylsulfinyl, particularly perhaloalkylsulfinyl, or haloalkylsulfonyl, particularly perhaloalkylsulfonyl.

$P_5$. A process of preparation of an ester compound of formula 4,

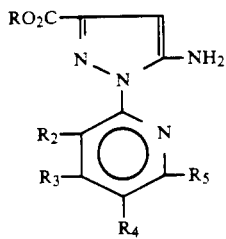

wherein, $R_2$, $R_3$, $R_4$ and $R_5$ are as defined in general formula (I) and R is $C_{1-4}$ lower alkyl, which comprises reacting a $C_{1-4}$ alkyl 2-oxo-3-cyanopropionate compound of formula 2, obtained by acid neutralization of its enolate salt, with a 2-pyridylhydrazine compound of formula 3, substituted by $R_2$ to $R_5$ as defined above, to give the compound of formula 4.

$P_6$. A process of preparation of a carboxamide compound of formula 9,

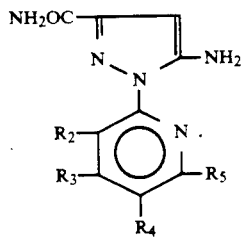

wherein, $R_2$, $R_3$, $R_4$ and $R_5$ are as defined in general formula (I), which comprises amidating with ammonia the ester compound of formula 4, obtained by the process $P_5$.

$P_7$. A process of preparation of a nitrile compound of formula 10,

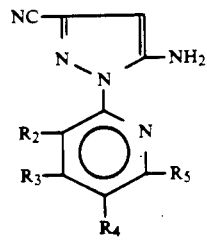

wherein, $R_2$, $R_3$, $R_4$ and $R_5$ are as defined in general formula (I), which comprises dehydrating with a dehydrating agent the carboxamide compound of formula 9, obtained by the process $P_6$.

$P_8$. A process of preparation of a compound of formula (I), wherein X, Y, Z, $R_2$, $R_3$, $R_4$ and $R_5$ are as defined in formula (I), which comprises reacting a compound of formula 4 according to the process of preparation of any of processes $P_1$ to $P_4$ for introduction of the X, Y and Z substituents.

$P_9$. A process of preparation of a compound of formula (I), wherein X, Y, Z, $R_2$, $R_3$, $R_4$ and $R_5$ are as defined in formula (I), which comprises reacting any one of intermediate compounds 4, 5, 6, 9, 10, 11, 12, 14, 19, 21, 22, 25 or (V) according to any of processes $P_1$ to $P_8$.

REPRESENTATIVE COMPOUNDS OF THE INVENTION

The compounds in TABLE 1 are illustrative of some of the preferred compounds within the purview of the above generic formula (I) or (IIa) or (IIb) and can be prepared by the herein described methods or processes of synthesis, by the appropriate selection of reactants, conditions and procedures, which are commonly known and apparent to one skilled in the art.

TABLE 1

REPRESENTATIVE PYRIDYL PYRAZOLES COMPOUNDS OF FORMULA (I)
SUBSTITUENT GROUPS

| No. | Z | X | Y | $R_2$ | $R_3$ | $R_4$ | $R_5$ |
|---|---|---|---|---|---|---|---|
| 1 | CN | Cl | $NH_2$ | Cl | H | $CF_3$ | H |
| 2 | CN | Cl | CN | Cl | H | $CF_3$ | H |
| 3 | CN | $NO_2$ | $NH_2$ | Cl | H | $CF_3$ | H |
| 4 | Cl | Cl | $NH_2$ | Cl | H | $CF_3$ | H |
| 5 | Cl | Cl | CN | Cl | H | $CF_3$ | H |
| 6 | Cl | $NO_2$ | $NH_2$ | Cl | H | $CF_3$ | H |
| 7 | Cl | $SCH_3$ | $NH_2$ | Cl | H | $CF_3$ | H |
| 8 | Cl | $SOCH_3$ | $NH_2$ | Cl | H | $CF_3$ | H |
| 9 | Cl | $SO_2CH_3$ | $NH_2$ | Cl | H | $CF_3$ | H |
| 10 | Cl | $SCF_3$ | $NH_2$ | Cl | H | $CF_3$ | H |
| 11 | Cl | $SOCF_3$ | $NH_2$ | Cl | H | $CF_3$ | H |
| 12 | Cl | $SO_2CF_3$ | $NH_2$ | Cl | H | $CF_3$ | H |
| 13 | Cl | $SCClF_2$ | $NH_2$ | Cl | H | $CF_3$ | H |
| 14 | Cl | $SOClF_2$ | $NH_2$ | Cl | H | $CF_3$ | H |
| 15 | Cl | $SO_2CClF_2$ | $NH_2$ | Cl | H | $CF_3$ | H |
| 16 | Cl | $SCCl_2F$ | $NH_2$ | Cl | H | $CF_3$ | H |
| 17 | Cl | $SOCCl_2F$ | $NH_2$ | Cl | H | $CF_3$ | H |
| 18 | Cl | $SO_2CCl_2F$ | $NH_2$ | Cl | H | $CF_3$ | H |
| 19 | Cl | $SCHF_2$ | $NH_2$ | Cl | H | $CF_3$ | H |
| 20 | Cl | $SOCHF_2$ | $NH_2$ | Cl | H | $CF_3$ | H |
| 21 | Cl | $SO_2CHF_2$ | $NH_2$ | Cl | H | $CF_3$ | H |
| 22 | Cl | $SCH_2F$ | $NH_2$ | Cl | H | $CF_3$ | H |
| 23 | Cl | $SCF_2CF_3$ | $NH_2$ | Cl | H | $CF_3$ | H |
| 24 | Cl | $SCF_3$ | H | Cl | H | $CF_3$ | H |
| 25 | Cl | $SOCF_3$ | H | Cl | H | $CF_3$ | H |
| 26 | Cl | $SO_2CF_3$ | H | Cl | H | $CF_3$ | H |
| 27 | Cl | $SCF_3$ | Br | Cl | H | $CF_3$ | H |
| 28 | Cl | $SOCF_3$ | Br | Cl | H | $CF_3$ | H |
| 29 | Cl | $SO_2CF_3$ | Br | Cl | H | $CF_3$ | H |
| 30 | Cl | $SCF_3$ | $NHCH_2OC_2H_5$ | Cl | H | $CF_3$ | H |
| 31 | Cl | $SCF_3$ | $SCH_3$ | Cl | H | $CF_3$ | H |
| 32 | Cl | $SCF_3$ | $NHCH_3$ | Cl | H | $CF_3$ | H |

TABLE 1-continued
REPRESENTATIVE PYRIDYL PYRAZOLES COMPOUNDS OF FORMULA (I)
SUBSTITUENT GROUPS

| No. | Z | X | Y | R2 | R3 | R4 | R5 |
|---|---|---|---|---|---|---|---|
| 33 | Cl | SCF$_3$ | NH$_2$ | Cl | H | Cl | H |
| 34 | Cl | SOCF$_3$ | NH$_2$ | Cl | H | Cl | H |
| 35 | Cl | SO$_2$CF$_3$ | NH$_2$ | Cl | H | Cl | H |
| 36 | Cl | SCH$_3$ | NH$_2$ | Cl | H | Cl | H |
| 37 | Cl | SCF$_3$ | H | Cl | H | Cl | H |
| 38 | Cl | SCF$_3$ | Br | Cl | H | Cl | H |
| 39 | Cl | SCF$_3$ | NH$_2$ | Cl | H | F | H |
| 40 | Cl | SOCF$_3$ | NHCH$_2$OC$_2$H$_5$ | Cl | H | Cl | H |
| 41 | Cl | SCF$_2$Cl | NHCH$_3$ | Cl | H | Cl | H |
| 42 | Cl | SOCF$_2$Cl | NH$_2$ | Cl | H | Cl | H |
| 43 | Cl | NO$_2$ | NH$_2$ | Cl | H | Cl | H |
| 44 | Cl | SCF$_3$ | CN | Cl | H | CF$_3$ | H |
| 45 | Cl | SCF$_3$ | SCH$_3$ | Cl | H | Cl | H |
| 46 | Cl | Cl | NH$_2$ | Cl | H | Cl | H |
| 47 | CN | SO$_2$CF$_3$ | Br | Cl | H | CF$_3$ | H |
| 48 | CN | SCF$_3$ | SCH$_3$ | Cl | H | CF$_3$ | H |
| 49 | CN | SOCF$_3$ | SCH$_3$ | Cl | H | CF$_3$ | H |
| 50 | CN | SO$_2$CF$_3$ | SC$_2$H$_5$ | Cl | H | CF$_3$ | H |
| 51 | CN | SO$_2$CF$_3$ | SO$_2$CH$_3$ | Cl | H | CF$_3$ | H |
| 52 | CN | SCF$_3$ | OCH$_3$ | Cl | H | CF$_3$ | H |
| 53 | CN | SOCF$_3$ | OCH$_3$ | Cl | H | CF$_3$ | H |
| 54 | CN | SO$_2$CF$_3$ | OCH$_3$ | Cl | H | CF$_3$ | H |
| 55 | CN | SCF$_3$ | NHCH$_3$ | Cl | H | CF$_3$ | H |
| 56 | CN | SO$_2$CF$_3$ | NHCH$_3$ | Cl | H | CF$_3$ | H |
| 57 | CN | SOCF$_3$ | NHCH$_3$ | Cl | H | CF$_3$ | H |
| 58 | CN | SCF$_3$ | N(C$_2$H$_5$)$_2$ | Cl | H | CF$_3$ | H |
| 59 | CN | SOCF$_3$ | N(CH$_3$)$_2$ | Cl | H | CF$_3$ | H |
| 60 | CN | SO$_2$CF$_3$ | N(CH$_3$)$_2$ | Cl | H | CF$_3$ | H |
| 61 | CN | SCF$_3$ | N(CH$_3$)$_3^+$ | Cl | H | CF$_3$ | H |
| 62 | CN | SCF$_3$ | NHCH$_2$CN | Cl | H | CF$_3$ | H |
| 63 | CN | SOCF$_3$ | NHCH$_2$CN | Cl | H | CF$_3$ | H |
| 64 | CN | SO$_2$CF$_3$ | NHCH$_2$CN | Cl | H | CF$_3$ | H |
| 65 | CN | SCF$_3$ | NHCH$_2$OC$_2$H$_5$ | Cl | H | CF$_3$ | H |
| 66 | CN | SCF$_3$ | NHCO$_2$C$_2$H$_5$ | Cl | H | CF$_3$ | H |
| 67 | CN | SCF$_3$ | NHCH$_2$CO$_2$C$_2$H$_5$ | Cl | H | CF$_3$ | H |
| 68 | CN | SCF$_3$ | NHCON(CH$_3$)$_2$ | Cl | H | CF$_3$ | H |
| 69 | CN | SCF$_3$ | N=CHOCH$_3$ | Cl | H | CF$_3$ | H |
| 70 | CN | SCClF$_2$ | Br | Cl | H | CF$_3$ | H |
| 71 | CN | SOCClF$_2$ | Br | Cl | H | CF$_3$ | H |
| 72 | CN | SO$_2$CClF$_2$ | Br | Cl | H | CF$_3$ | H |
| 73 | CN | SCClF$_2$ | SCH$_3$ | Cl | H | CF$_3$ | H |
| 74 | CN | SOCClF$_2$ | SCH$_3$ | Cl | H | CF$_3$ | H |
| 75 | CN | SO$_2$CClF$_2$ | SCH$_3$ | Cl | H | CF$_3$ | H |
| 76 | CN | SCClF$_2$ | SOCH$_3$ | Cl | H | CF$_3$ | H |
| 77 | CN | SCClF$_2$ | SO$_2$CH$_3$ | Cl | H | CF$_3$ | H |
| 78 | CN | SCClF$_2$ | NHC$_2$H$_5$ | Cl | H | CF$_3$ | H |
| 79 | CN | SCClF$_2$ | N(CH$_3$)$_2$ | Cl | H | CF$_3$ | H |
| 80 | CN | SOCClF$_2$ | N(CH$_3$)$_2$ | Cl | H | CF$_3$ | H |
| 81 | CN | SO$_2$CClF$_2$ | N(CH$_3$)$_2$ | Cl | H | CF$_3$ | H |
| 82 | CN | SCClF$_2$ | N(CH$_3$)$_3^+$ | Cl | H | CF$_3$ | H |
| 83 | CN | SCClF$_2$ | NHCH$_2$CN | Cl | H | CF$_3$ | H |
| 84 | CN | SCClF$_2$ | NHCH$_2$OC$_2$H$_5$ | Cl | H | CF$_3$ | H |
| 85 | CN | SOCClF$_2$ | NHCH$_2$OC$_2$H$_5$ | Cl | H | CF$_3$ | H |
| 86 | CN | SO$_2$CClF$_2$ | NHCH$_2$OC$_2$H$_5$ | Cl | H | CF$_3$ | H |
| 87 | CN | SCClF$_2$ | NHCO$_2$C$_2$H$_5$ | Cl | H | CF$_3$ | H |
| 88 | CN | SOCClF$_2$ | NHCO$_2$C$_2$H$_5$ | Cl | H | CF$_3$ | H |
| 89 | CN | SO$_2$CClF$_2$ | NHCO$_2$C$_2$H$_5$ | Cl | H | CF$_3$ | H |
| 90 | CN | SCClF$_2$ | NHCOCH$_3$ | Cl | H | CF$_3$ | H |
| 91 | CN | SOCClF$_2$ | NHCOCH$_3$ | Cl | H | CF$_3$ | H |
| 92 | CN | SO$_2$CClF$_2$ | NHCOCH$_3$ | Cl | H | CF$_3$ | H |
| 93 | CN | SCClF$_2$ | NHCON(CH$_3$)$_2$ | Cl | H | CF$_3$ | H |
| 94 | CN | SCClF$_2$ | N=CHOCH$_3$ | Cl | H | CF$_3$ | H |
| 95 | CN | SOCClF$_2$ | N=CHOCH$_3$ | Cl | H | CF$_3$ | H |
| 96 | CN | SO$_2$CClF$_2$ | N=CHOCH$_3$ | Cl | H | CF$_3$ | H |
| 97 | CN | SOCCl$_2$F | NH$_2$ | Cl | H | CF$_3$ | H |
| 98 | CN | SCCl$_2$F | H | Cl | H | CF$_3$ | H |
| 99 | CN | SOCCl$_2$F | H | Cl | H | CF$_3$ | H |
| 100 | CN | SO$_2$CCl$_2$F | H | Cl | H | CF$_3$ | H |
| 101 | CN | SCCl$_2$F | Br | Cl | H | CF$_3$ | H |
| 102 | CN | SOCCl$_2$F | Br | Cl | H | CF$_3$ | H |
| 103 | CN | SO$_2$CCl$_2$F | Br | Cl | H | CF$_3$ | H |
| 104 | CN | SCCl$_2$F | SCH$_3$ | Cl | H | CF$_3$ | H |
| 105 | CN | SOCCl$_2$F | SCH$_3$ | Cl | H | CF$_3$ | H |
| 106 | CN | SO$_2$CCl$_2$F | SCH$_3$ | Cl | H | CF$_3$ | H |
| 107 | CN | SCCl$_2$F | SOCH$_3$ | Cl | H | CF$_3$ | H |
| 108 | CN | SCCl$_2$F | SO$_2$CH$_3$ | Cl | H | CF$_3$ | H |
| 109 | CN | SCCl$_2$F | NHCH$_3$ | Cl | H | CF$_3$ | H |
| 110 | CN | SCCl$_2$F | N(C$_2$H$_5$)$_2$ | Cl | H | CF$_3$ | H |
| 111 | CN | SCCl$_2$F | N(CH$_3$)$_3^+$ | Cl | H | CF$_3$ | H |
| 112 | CN | SCCl$_2$F | NHCH$_2$CN | Cl | H | CF$_3$ | H |
| 113 | CN | SOCCl$_2$F | NHCH$_2$CN | Cl | H | CF$_3$ | H |
| 114 | CN | SO$_2$CCl$_2$F | NHCH$_2$CN | Cl | H | CF$_3$ | H |
| 115 | CN | SOCCl$_2$F | NHCH$_2$OC$_2$H$_5$ | Cl | H | CF$_3$ | H |
| 116 | CN | SO$_2$CCl$_2$F | NHCH$_2$OC$_2$H$_5$ | Cl | H | CF$_3$ | H |
| 117 | CN | SCCl$_2$F | NHCO$_2$C$_2$H$_5$ | Cl | H | CF$_3$ | H |
| 118 | CN | SOCCl$_2$F | NHCOCH$_3$ | Cl | H | CF$_3$ | H |
| 119 | CN | SO$_2$CCl$_2$F | NHCONHCH$_3$ | Cl | H | CF$_3$ | H |
| 120 | CN | SCCl$_2$F | N=CHOC$_2$H$_5$ | Cl | H | CF$_3$ | H |
| 121 | CN | SOCH$_3$ | H | Cl | H | CF$_3$ | H |
| 122 | CN | SO$_2$CH$_3$ | H | Cl | H | CF$_3$ | H |
| 123 | CN | SOCH$_3$ | Br | Cl | H | CF$_3$ | H |
| 124 | CN | SO$_2$CH$_3$ | Br | Cl | H | CF$_3$ | H |
| 125 | CN | SCH$_3$ | SCH$_3$ | Cl | H | CF$_3$ | H |
| 126 | CN | SOCH$_3$ | SOCH$_3$ | Cl | H | CF$_3$ | H |
| 127 | CN | SO$_2$CH$_3$ | SO$_2$CH$_3$ | Cl | H | CF$_3$ | H |
| 128 | CN | SCH$_3$ | N(CH$_3$)$_2$ | Cl | H | CF$_3$ | H |
| 129 | CN | SCH$_3$ | NHCH$_2$CN | Cl | H | CF$_3$ | H |
| 130 | CN | SOCH$_3$ | NHCH$_2$OC$_2$H$_5$ | Cl | H | CF$_3$ | H |
| 131 | CN | SO$_2$CH$_3$ | NHCO$_2$C$_2$H$_5$ | Cl | H | CF$_3$ | H |
| 132 | CN | SCH$_3$ | NHCOCH$_3$ | Cl | H | CF$_3$ | H |
| 133 | CN | SOCH$_3$ | N=CHOC$_2$H$_5$ | Cl | H | CF$_3$ | H |
| 134 | CN | SCHF$_2$ | NH$_2$ | Cl | H | CF$_3$ | H |
| 135 | CN | SO$_2$CHF$_2$ | NH$_2$ | Cl | H | CF$_3$ | H |
| 136 | CN | SCHF$_2$ | H | Cl | H | CF$_3$ | H |
| 137 | CN | SOCHF$_2$ | H | Cl | H | CF$_3$ | H |
| 138 | CN | SO$_2$CHF$_2$ | H | Cl | H | CF$_3$ | H |
| 139 | CN | SCHF$_2$ | Br | Cl | H | CF$_3$ | H |
| 140 | CN | SCHF$_2$ | SCH$_3$ | Cl | H | CF$_3$ | H |
| 141 | CN | SCHF$_2$ | SCH$_3$ | Cl | H | CF$_3$ | H |
| 142 | CN | SCHF$_2$ | SOCH$_3$ | Cl | H | CF$_3$ | H |
| 143 | CN | SCHF$_2$ | NHCO$_2$C$_2$H$_5$ | Cl | H | CF$_3$ | H |
| 144 | CN | SOCHF$_2$ | NHCONHCH$_3$ | Cl | H | CF$_3$ | H |
| 145 | CN | SO$_2$CHF$_2$ | NHCH$_2$OC$_2$H$_5$ | Cl | H | CF$_3$ | H |
| 146 | CN | SCHF$_2$ | N=CHOC$_2$H$_5$ | Cl | H | CF$_3$ | H |
| 147 | CN | SCH$_2$F | NH$_2$ | Cl | H | CF$_3$ | H |
| 148 | CN | SOCH$_2$F | NH$_2$ | Cl | H | CF$_3$ | H |
| 149 | CN | SO$_2$CH$_2$F | NH$_2$ | Cl | H | CF$_3$ | H |
| 150 | CN | SCH$_2$F | H | Cl | H | CF$_3$ | H |
| 151 | CN | SOCH$_2$F | Br | Cl | H | CF$_3$ | H |
| 152 | CN | SO$_2$CH$_2$F | N(CH$_3$)$_2$ | Cl | H | CF$_3$ | H |
| 153 | CN | SCH$_2$F | SCH$_3$ | Cl | H | CF$_3$ | H |
| 154 | CN | SOCH$_2$F | SO$_2$CH$_3$ | Cl | H | CF$_3$ | H |
| 155 | CN | SO$_2$CH$_2$F | NHCH$_2$OC$_2$H$_5$ | Cl | H | CF$_3$ | H |
| 156 | CN | SCHF$_2$ | NHCO$_2$C$_2$H$_5$ | Cl | H | CF$_3$ | H |
| 157 | CN | SOCF$_3$ | NH$_2$ | Cl | H | Cl | H |
| 158 | CN | SO$_2$CF$_3$ | NH$_2$ | Cl | H | Cl | H |
| 159 | CN | SCClF$_2$ | NH$_2$ | Cl | H | Cl | H |
| 160 | CN | SOCClF$_2$ | NH$_2$ | Cl | H | Cl | H |
| 161 | CN | SO$_2$CClF$_2$ | NH$_2$ | Cl | H | Cl | H |
| 162 | CN | SCCl$_2$F | NH$_2$ | Cl | H | Cl | H |
| 163 | CN | SOCCl$_2$F | NH$_2$ | Cl | H | Cl | H |
| 164 | CN | SO$_2$CCl$_2$F | NH$_2$ | Cl | H | Cl | H |
| 165 | CN | SOCH$_3$ | NH$_2$ | Cl | H | Cl | H |
| 166 | CN | SO$_2$CH$_3$ | NH$_2$ | Cl | H | Cl | H |
| 167 | CN | SCHF$_2$ | NH$_2$ | Cl | H | Cl | H |
| 168 | CN | SCH$_2$F | NH$_2$ | Cl | H | Cl | H |
| 169 | CN | Cl | NH$_2$ | Cl | H | Cl | H |
| 170 | CN | NO$_2$ | NH$_2$ | Cl | H | Cl | H |
| 171 | CN | SCF$_3$ | CN | Cl | H | CF$_3$ | H |
| 172 | CN | SCF$_3$ | SCH$_3$ | Cl | H | Cl | H |
| 173 | CN | SCF$_3$ | NHCH$_2$OC$_2$H$_5$ | Cl | H | Cl | H |
| 174 | CN | SCF$_3$ | NH$_2$ | CF$_3$ | H | CF$_3$ | H |
| 175 | CN | SOCCl$_2$F | NH$_2$ | CF$_3$ | H | CF$_3$ | H |
| 176 | CN | SO$_2$CF$_2$Cl | Br | CF$_3$ | H | CF$_3$ | H |
| 177 | CN | SOCF$_3$ | NH$_2$ | H | H | NO$_2$ | H |
| 178 | CN | SCF$_3$ | NH$_2$ | Cl | H | NO$_2$ | H |
| 179 | CN | SO$_2$CF$_3$ | NH$_2$ | Cl | H | CN | H |
| 180 | CN | SOCClF$_2$ | NH$_2$ | Cl | H | CH$_3$ | H |
| 181 | CN | SO$_2$CClF$_2$ | NH$_2$ | H | H | OCF$_3$ | H |
| 182 | CN | SCl$_2$F | NH$_2$ | F | H | F | H |
| 183 | CN | SOCCl$_2$F | NH$_2$ | Cl | H | OCH$_3$ | H |
| 184 | CN | SO$_2$CCl$_2$F | NH$_2$ | H | H | H | F |
| 185 | CN | SCF$_3$ | NH$_2$ | H | H | CN | H |

TABLE 1-continued

REPRESENTATIVE PYRIDYL PYRAZOLES
COMPOUNDS OF FORMULA (I)
SUBSTITUENT GROUPS

| No. | Z | X | Y | $R_2$ | $R_3$ | $R_4$ | $R_5$ |
|---|---|---|---|---|---|---|---|
| 186 | CN | $SCF_3$ | $NH_2$ | H | H | H | Cl |

The following EXAMPLES 1 to 27 further illustrate some of the more preferred compounds of formula (I) and (II) of the invention that were prepared. Details of typical methods of synthesis utilized in the preparation of intermediates and compounds of the invention are specifically provided below for compounds of EXAMPLES 1 to 7. The other compounds were prepared using similar methods of synthesis or modifications thereof of the detailed procedures as applicable to a given compound. These compound examples are listed in TABLE 2, wherein $R_2$ is Cl, $R_3$ and $R_5$ are H, and $R_1$, n, Y, and $R_4$ are as defined. Reported melting points for compounds represent the average value of an observed melting point range determined for a compound or furthermore represent the average value of a number of separate melting point determinations. Additionally, one or more spectroscopic analyses (IR, NMR, GC/MS, etc.) have been performed on each compound for characterization and confirmation of the chemical structure.

EXAMPLE 1

Preparation of
1-[2-(3-chloro-5-trifluoromethyl)pyridyl]-3-cyano-4-chlorodifluoromethylsulfenyl-5-aminopyrazole Reaction Scheme 1-PATH A a) Preparation of intermediate: 1-[2-(3-chloro-5-trifluoromethyl)pyridyl]-3-ethoxycarbonyl-5-aminopyrazole.

In a large beaker was placed 250 ml of $H_2O$, 250 g of ice and the sodium salt of ethyl-2-oxy-3-cyano-2-propenoate (26.8 g, 164.8 mmol). The pH of the suspension was adjusted to 2 with dilute aqueous $H_2SO_4$. Sodium chloride (40 g) was added and the solution was extracted with EtOAC. The organic layer was dried over $MgSO_4$, filtered and concentrated. The crude acyl ester was immediately diluted with EtOH (175 ml) and added to a round-bottom flask containing 2-hydrazino-3-chloro-5-trifluoromethylpyridine (22.5 g, 106.3 mmol). The reaction was heated at reflux for two hours, then sodium bicarbonate (9.8 g, 116 mmol) was added and refluxing continued for two hours. At this time, the reaction mixture was cooled, diluted with 600 ml of ether, and filtered through a pad of Celite. The filtrates were washed with $H_2O$, 10% aqueous HCl and $H_2O$. The organics were dried over $MgSO_4$, filtered, and concentrated. The resulting solid was recrystalized from EtOH and washed twice with pet ether to give the desired product as a dark tan solid (25.63 g, 72% yield), m.p. 157.5° C.

$^1$H NMR (CDCl$_3$)-δ1.35 (t, 3H, J=7 Hz), 4.38 (q, 2H, J=7 Hz), 4.62 (br s, 2H), 6.12 (s, 1H), 8.19 (s, 1H), and 8.68 (s, 1H).

b) Preparation of intermediate: 1-[2-(3-chloro-5-trifluoromethyl)pyridyl]-3-ethoxycarbonyl-4-chlorodifluoromethylsulfenyl)-5-aminopyrazole.

A round-bottom flask equipped with a condenser, under $N_2$, was charged with the pyrazole (EXAMPLE 1a) (10.0 g, 29.9 mmol) in 30 ml of acetic acid. Then chlorodifluoromethylsulfenyl chloride (3.3 ml, 32.9 mmol) was added all at once. The reaction was stirred overnight at room temperature. A TLC analysis showed no starting material was present. The reaction was diluted with $CH_2Cl_2$ (200 ml) and washed with $H_2O$ (2×100 ml), aqueous sodium bicarbonate (2×50 ml), and saturated aqueous NaCl. The organic layer was dried (MgSO$_4$), filtered, and concentrated to give 13.08 g (97%) of the desired product, m.p. 142.5°.

$^1$H NMR (CDCl$_3$)-δ1.39 (t, 3H, J=7 Hz), 4.42 (q, 2H, J=7 Hz), 5.4 (br s, 2H), 8.2 (s, 1H), and 8.72 (s, 1H).

c) Preparation of 1-[2-(3-chloro-5-trifluoromethyl)pyridyl]-3-cyano-4-chlorodifluoromethylsulfenyl-5-aminopyrazole.

A fresh solution of dimethylaluminum amide was prepared as described in the literature (*Tetrahedron Letters*, 1979, 4907). The pyrazole (EXAMPLE 1b) (12.1 g, 26.8 mmol) was dissolved in 200 ml of $CH_2Cl_2$ in a round-bottom flask equipped with a condenser under a $N_2$ atmosphere. The dimethylaluminum amide (45 ml, 1.2M in $CH_2Cl_2$) was added and the reaction was stirred at room temperature for one half hour and heated at reflux overnight. The reaction was cooled and poured into a large beaker. Ice and $H_2O$ (300 ml) were carefully added. Then 10% aqueous HCl was added until the aqueous layer was acidic. The layers were separated and the aqueous layer was extracted with CHCl$_3$ (200 ml) and EtOAC (100 ml). The combined organic layers were washed with $H_2O$ and saturated aqueous NaCl, dried over $MgSO_4$, filtered, and concentrated to give 10.79 g of a tan solid.

The tan solid was placed in a round-bottom flask with 60 ml of POCl$_3$. The reaction was heated at reflux for five hours and stirred at room temperature overnight. The POCl$_3$ was then stripped off in vacuo. To the residue was added 300 ml of $H_2O$ and 200 ml of EtOAC. The layers were separated and the aqueous layer was extracted with EtOAC. The combined organics were washed with saturated NaHCO$_3$, dried over MgSO$_4$, and concentrated to give 7.48 g of the crude product. The aqueous layer was adjusted to pH 8 with 10% aqueous NaOH and extracted with EtOAC to yield another 3.14 g of crude product.

Flash chromatography on silica gel (eluent 20% $CH_2Cl_2$/hexane to 75% $CH_2Cl_2$/hexane) gave the desired pure product in 25% yield, m.p. 122° C.

$^1$H NMR (CDCl$_3$)-δ5.76 (br s, 2H), 8.26 (s, 1H), and 8.73 (s, 1H).

EXAMPLE 2

Preparation of
1-[2-(3-chloro-5-trifluoromethyl)pyridyl]-3-cyano-4-chlorodifluoromethylsulfinyl-5-aminopyrazole A round-bottom flask equipped with a condenser, under $N_2$, was charged with 1-[2-(3-chloro-5-trifluoromethyl)pyridyl]-3-cyano-4-chlorodifluoromethylsulfenyl-5-aminopyrazole (0.5 g, 1.24 mmol), TFA (10 ml) and 30% $H_2O_2$ (120 μl) and the reaction was stirred at room temperature for six days. The reaction mixture as then poured onto ice (25 g) and extracted with EtOAC. The organic layer was washed with 10% aqueous Na$_2$S$_2$O$_3$ (1×), aqueous NaHCO$_3$ (4×), and $H_2O$, dried over MgSO$_4$, filtered, and concentrated. The crude sulfoxide was purified by flash chromatography on silica gel (eluent 75% $CH_2Cl_2$/hexane) to give the desired product (0.43 g, 83%) as a white crystaline solid, m.p. 155.5° C.

$^1$H NMR (CDCl$_3$)-δ7.00 (br s, 2H), 8.33 (s, 1H), and 8.76 (s, 1H).

EXAMPLE 3

Preparation of
1-[2-(3-chloro-5-trifluoromethyl)pyridyl]-3-cyano-4-chlorodifluoromethylsulfonyl-5-aminopyrazole A round-bottom flask equipped with a condenser under a N$_2$ atmosphere was charged with 1-[2-(3-chloro-5-trifluoromethyl)pyridyl]-3-cyano-4-chlorodifluoromethylsulfenyl-5-aminopyrazole (0.5 g, 1.24 mmol) in 25 ml of CHCl$_3$. m-Chloroperoxybenzoic acid (80-85% purity), 0.75 g, 3 equiv.) was added to the reaction all at once and heated at reflux overnight. The reaction was diluted with 50 ml of CHCl$_3$ and washed with 10% aqueous NaOH (2×25 ml), H$_2$O (25 ml), dried over MgSO$_4$, filtered, and concentrated. The crude sulfone was recrystallized from CH$_2$Cl$_2$: hexane (1:9) to give 0.35 g (65%) of a white solid, m.p. 154.5° C.

$^1$H NMR (CDCl$_3$)-δ6.58 (br s, 2H), 8.32 (s, 1H), and 8.74 (s, 1H).

EXAMPLE 4

Preparation of
1-[2-(3-chloro-5-trifluoromethyl)pyridyl]-3-cyano-4-chlorodifluoromethylsulfenylpyrazole A round-bottom flask with a condenser under a N$_2$ atmosphere was charged with the amino pyrazole, EXAMPLE 1c, (1.32 g, 3.27 mmol), t-butyl nitrite (1.9 ml, 16.3 mmol) and 60 ml of THF. The reaction mixture was stirred at room temperature for four hours. The solvents were removed in vacuo and the oily residue was purified by flash chromatography on silica gel (eluent 75% CH$_2$Cl$_2$/hexane) to give 1.02 g (80%) of an oil. The oil was crystallized from pet ether to give a pale yellow solid, m.p. 53° C.

$^1$H NMR (CDCl$_3$)-δ8.26 (s, 1H), 8.63 (s, 1H), and 8.73 (s, 1H).

EXAMPLE 5

Preparation of
1-[2-(3-chloro-5-trifluoromethyl)pyridyl]-3-cyano-4-dichlorofluoromethylsulfenyl-5-aminopyrazole Reaction Scheme 1-Path B.

a) Preparation of intermediate: 1-[2-(3-chloro-5-trifluoromethyl)pyridyl]-3-aminocarbonyl-5-aminopyrazole.

A round-bottom flask with a condenser under N$_2$ was charged with 1-[2-(3-chloro-5-trifluoromethyl)pyridyl]-3-ethoxycarbonyl-5-aminopyrazole (25 g, 74.7 mmol), 100 ml aqueous NH$_4$OH, 300 ml MeOH and 1 ml of H$_2$O. The reaction was stirred at room temperature for three days. Ice was then added to the reaction mixture and the aqueous solution was carefully acidified to pH 1-2 with 10% HCl. The aqueous layer was extracted with CH$_2$Cl$_2$ (3×) and EtOAC (1×). The organic layers were dried over MgSO$_4$, filtered, and concentrated to give 20.4 g (90%) of a tan solid which was used as is in the next reaction.

$^1$H NMR (CDCl$_3$/DMSO-d$_6$)-δ5.3 (br s, 2H), 6.02 (s, 1H), 6.48 (br s, 1H), 6.75 (br s, 1H), 8.13 (m, 1H), and 8.62 (m, 1H).

b) Preparation of intermediate: 1-[2-(3-chloro-5-trifluoromethyl)pyridyl]-3-cyano-5-aminopyrazole.

The amide prepared in EXAMPLE 5a (13.4 g, 43.8 mmol) was placed in a round-bottom flask equipped with an addition funnel, thermometer, and N$_2$ inlet. To this was added THF (75 ml) and pyridine (11 ml, 135.8 mmol) and the solution was cooled in an ice bath. Trifluoroacetic anhydride (13 ml, 91.98 mmol) was slowly added via the addition funnel maintaining the temperature below ~10° C. The solution was allowed to slowly warm and stirred overnight. The reaction was diluted with CHCl$_3$ (150 ml), washed with H$_2$O (2×50 ml), and washed with 10% aqueous HCl (50 ml). The organic layer was dried over MgSO$_4$, filtered, and concentrated to give 17.03 g of a dark oil which was placed in a flask with 300 ml of MeOH and 100 ml of aqueous NH$_4$OH and refluxed for eight hours. The solvents were evaporated and the residue was dissolved in EtOAC, washed with H$_2$O and saturated NaCl, dried over MgSO$_4$, and concentrated. The crude product was washed with cold CH$_2$Cl$_2$ and collected on a funnel to give 4.3 g of a white tan solid. Concentration of the filtrate and washing with cold CH$_2$Cl$_2$ yielded a further 1.7 g (total 48%) of pure product.

$^1$H NMR (CDCl$_3$/DMSO-d$_6$)-δ5.8 (br s, 2H), 5.9 (s, 1H), 8.34 (m, 1H), and 8.73 (m, 1H).

c) Preparation of 1-[2-(3-chloro-5-trifluoromethyl)pyridyl]-3-cyano-4-dichlorofluoromethylsulfenyl-5-aminopyrazole.

A round-bottom flask with reflux condenser and N$_2$ inlet was charged with the amino nitrile, EXAMPLE 5b, (3.58 g, 12.5 mmol) and 30 ml acetic acid. Dichlorofluoromethylsulfenyl chloride (1.44 ml, 13.7 mmol) was added via syringe and the reaction was heated at reflux for two hours and stirred at room temperature overnight. Methylene chloride was added and the organic phase was washed with H$_2$O, saturated aqueous NaHCO$_3$ (2×), and H$_2$O. The organic layer was dried over MgSO$_4$, filtered, and concentrated. The crude solid was purified by flash chromatography on silica gel (eluent 8:1 hexane/EtOAC) to give 3.19 g (61%) of desired product, m.p. 133° C.

$^1$H NMR (CDCl$_3$)-δ5.76 (br s, 2H), 8.22 (d, 1H, J=2 Hz), and 8.66 (d, 1H, J=2 Hz).

EXAMPLE 6

Preparation of
1-[2-(3-chloro-5-trifluoromethyl)pyridyl]-3-cyano-4-dichlorofluoromethylsulfenyl-5-ethoxymethylaminopyrazole A round-bottom flask with thermometer and a simple distillation set up was charged with the starting amino pyrazole (EXAMPLE 5c) (1.0 g, 2.4 mmol) and 25 ml of triethylorthoformate heated at boiling point overnight. The triethylorthoformate was removed in vacuo and the residue dried in a vacuum oven. An NMR indicated the desired ethoxymethylideneimino intermediate. The residue was dissolved in EtOH (20 ml) in a round-bottom flask under N$_2$ and cooled to 5° C. in an ice/salt bath. Sodium borohydride (24 mg, 0.63 mmol) was added and the reaction stirred at 5° C. for three hours. The reaction was quenched by the addition of saturated NH$_4$Cl. The solvents were removed in vacuo to give a yellow oil. The oil was purified by flash chromatography on silica gel (eluent 7:1 hexane/EtOAC) and yielded 570 mg (55%) of the desired product as off-white solid, m.p. 118.5° C.

$^1$H NMR (CDCl$_3$)-δ1.06 (t, 3H, J=7 Hz), 3.38 (q, 2H, J=7 Hz), 4.75 (d, 2H, J=7 Hz), 6.7 (br t, 1H, J=7 Hz), 8.2 (d, 1H, J=2 Hz), and 8.7 (d, 1H, J=2 Hz).

EXAMPLE 7

Preparation of 1-[2-(3-chloro-5-trifluoromethyl)pyridyl]-3-cyano-4-trifluoromethylsulfenyl-5-bromopyrazole To a solution of 1-[2-(3-chloro-5-trifluoromethyl)-pyridyl]-3-cyano4-4-trifluoromethylsulfenyl-5-aminopyrazole (1.0 g, 2.58 mmol) in 25 ml of bromoform was added t-butylnitrite (1.5 ml, 12.9 mmol). The reaction was stirred at room temperature overnight. The bromoform was removed in vacuo and the oily residue was purified by flash chromatography on silica gel (eluent: 50% $CH_2Cl_2$/hexane) to give 1.06 g (91%) of the desired product, m.p. 54.5° C.

$^1$H NMR ($CDCl_3$)-δ8.31 (m, 1H), and 8.90 (m, 1H).

Using similar procedures to those of EXAMPLES 1-7, there were obtained EXAMPLES 8-27.

TABLE 2

ADDITIONAL SYNTHESIZED 1-PYRIDYL PYRAZOLE COMPOUNDS OF FORMULA (II), WHEREIN $R_2$ is Cl and $R_3$ and $R_5$ ARE H

| CMPD. OF EXAMPLE | $R_1$ | n | Y | $R_4$ | M.P. (°C.) |
|---|---|---|---|---|---|
| 8 | $CF_3$ | 0 | $NH_2$ | $CF_3$ | 110 |
| 9 | $CF_3$ | 1 | $NH_2$ | $CF_3$ | 141 |
| 10 | $CF_3$ | 2 | $NH_2$ | $CF_3$ | 161.5 |
| 11 | $CF_3$ | 0 | H | $CF_3$ | 51.5 |
| 12 | $CF_3$ | 1 | H | $CF_3$ | 101.5 |
| 13 | $CF_3$ | 2 | H | $CF_3$ | 82.5 |
| 14 | $CHF_2$ | 1 | $NH_2$ | $CF_3$ | 181.5 |
| 15 | $CF_3$ | 1 | Br | $CF_3$ | 115.5 |
| 16 | $CF_2Cl$ | 1 | H | $CF_3$ | 53.5 |
| 17 | $CF_2Cl$ | 2 | H | $CF_3$ | 85.5 |
| 18 | $CCl_2F$ | 2 | $NH_2$ | $CF_3$ | 140.5 |
| 19 | $CH_3$ | 0 | $NHCOCF_3$ | $CF_3$ | 139 |
| 20 | $CH_3$ | 0 | $NH_2$ | $CF_3$ | 132 |
| 21 | $CH_3$ | 1 | $NH_2$ | $CF_3$ | 169 |
| 22 | $CH_3$ | 2 | $NH_2$ | $CH_3$ | 187.5 |
| 23 | $CH_3$ | 0 | H | $CF_3$ | 85 |
| 24 | $CH_3$ | 0 | Br | $CF_3$ | 62.5 |
| 25 | $CH_3$ | 0 | $NH_2$ | Cl | 169 |
| 26 | $CF_3$ | 0 | $NH_2$ | Cl | OIL |
| 27 | $CF_3$ | 2 | $SCH_3$ | $CF_3$ | 110.5 |

EXAMPLE 28

MITICIDE, INSECTICIDE, APHICIDE, AND NEMATICIDE USE

The following test procedures, using the compounds of EXAMPLES 1-27, were conducted to determine the pesticidal use and activity of compounds of the invention against: mites; certain insects, including aphids, two species of caterpillar, a fly, and two species of beetle larvae (one foliar feeding and the other root feeding); and nematodes. The specific species tested were as follows:

| GENUS, SPECIES | COMMON NAME | (ABBREVIATION) |
|---|---|---|
| Tetranychus urticae | twospotted spider mite | TSM |
| Aphis nasturtii | buckthorn aphid | BA |
| Spodoptera eridania | southern armyworm | SAW |
| Epilachna varivestis | Mexican bean beetle | MBB |
| Musca domestica | housefly | HF |
| Diabrotica u. howardi | southern corn rootworm | SCRW |
| Meloidogyne incognita | southern root-knot nematode | SRKN |
| Aphis gossypii | cotton aphid | CA |
| Schizaphis graminum | greenbug (aphid) | GB |
| Nephotettix cincticeps | green leaf hopper | GLH |
| Nilaparvata lugens | brown plant hopper | BPH |
| Heliothis virescens | tobacco budworm | TBW |

Formulations:

The test compounds (EXAMPLES 1-27) were formulated for use according to the following methods used for each of the test procedures.

For mite, aphid, southern armyworm, Mexican bean beetle, and tobacco budworm tests, a solution or suspension was prepared by adding 10 mg of the test compound to a solution of 160 mg of dimethylformamide, 838 mg of acetone, 2 mg of a 3:1 ratio of Triton X-172:Triton X-152 (respectively, mainly anionic and nonionic low foam emulsifiers which are each anhydrous blends of alkylaryl polyether alcohols with organic sulfonates), and 98.99 g of water. The result was a concentration of 100 ppm of the test compound.

For housefly tests, the formulation was initially prepared in a similar manner to the above, but in 16.3 g of water with corresponding adjustment of other components, providing a 200 ppm concentration. Final dilution with an equal volume of a 20% by weight aqueous solution of sucrose provided a 100 ppm concentration of the test compound. When necessary, sonication was provided to insure complete dispersion.

For southern corn rootworm tests, a solution or suspension was prepared in the same manner as that used for the initial 200 ppm concentration for housefly. Aliquots of this 200 ppm formulation were then used by dilution with water according to the required test concentration.

For southern root-knot nematode and systemic tests for southern armyworm, cotton aphid, and greenbug, a stock solution or suspension was prepared by adding 15 mg of the test compound to 250 mg of dimethylformamide, 1250 mg of acetone and 3 mg of the emulsifier blend referenced above. Water was then added to bring the total volume to 45 ml and a test compound concentration of 333 ppm. When necessary, sonication was provided to insure complete dispersion.

For the green leaf hopper and brown plant hopper tests, a stock solution or suspension at 100 ppm was prepared adding 10 mg of the test compound to a 50% aqueous acetone solution and sonicated as necessary. Dilutions as required with 50% aqueous acetone provided the required test concentration.

Test Procedures:

The above formulated test compounds were then evaluated for their pesticidal activity at the specified concentrations, in ppm (parts per million) by weight, according to the following test procedures:

Twospotted spider mite: Leaves infested with adult and nymphal stages of the two-spotted spider mite, obtained from a stock culture were placed on the primary leaves of two bean plants growing in a 6 cm. peat pot. A sufficient number of mites (150-200) for testing were transferred to the fresh plants within a period of twenty-four hours. The potted plants (one pot per compound) were placed on a revolving turntable and sprayed, sufficient to wet the plants to runoff, with 100 ml of the 100 ppm test compound formulation by use of a DeVilbiss spray gun set at 40 psig. air pressure. As an untreated control, 100 ml of the water-acetone-DMF-emulsifier solution, containing no test compound, were also sprayed on infested plants. A treated control with a commercial technical compound, either dicofol or hexythiazox, formulated in the same manner, was tested as a standard. The sprayed plants were held for six days, after which a mortality count of motile forms was made.

Twospotted spider mite (ovicide test): Eggs were obtained from adults of the twospotted spider mite from a stock culture. Heavily infested leaves from the stock culture were placed on uninfested bean plants. Females were allowed to oviposit for a period of about 24 hours, after which the leaves of the plant were dipped into a solution of TEPP (tetraethyl diphosphate) in order to kill the motile forms and prevent additional egg laying. This dipping procedure, which was repeated after the plants dried, did not affect the viability of the eggs. The potted plants (one pot per compound) were placed on a revolving turntable and sprayed, sufficient to wet the plants to runoff, with 100 ml of the 100 ppm test compound formulation by use of a DeVilbiss spray gun set at 40 psig. air pressure. As an untreated control, 100 ml of the water-acetone-DMF-emulsifier solution, containing no test compound, were also sprayed on infested plants. A treated control with a commercial technical compound, typically demeton, formulated in the same manner, was tested as a standard. The sprayed plants were held for seven days, after which a mortality count of egg forms was made along with notations on residual activity on hatched larvae.

Buckthorn aphid: Adult and nymphal stages of buckthorn aphid were reared on potted dwarf nasturtium plants. The potted plants (one pot per compound tested) infested with 100–150 aphids, were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on infested plants. A treated control with a commercial technical compound, malathion, formulated in the same manner, was tested as a standard. After spraying, the pots were stored for one day after which the dead aphids were counted.

Southern armyworm: Potted bean plants, were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar southern armyworm larvae were introduced into each cup which was closed and held for five days. Larvae which were unable to move the length of the body, even upon stimulation by prodding, were considered dead.

Tobacco budworm: Potted cotton plants were placed on a revolving turntable and sprayed with 100 ml of the 100 ppm test compound formulation by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic dishes containing a piece of filter paper and a moistened dental wick. One randomly selected second instar tobacco budworm larva was then introduced into each cup which was closed and held for five days. Larvae unable to move the length of their body, even upon stimulation by prodding, were considered dead.

Greenleaf hopper and brown plant hopper: Potted rice plants were placed on a revolving turntable and sprayed to runoff with 60 ml of 0.5 to 10 ppm test compound formulation by use of a turntable sprayer. As an untreated control, an equal volume of aqueous acetone (50:50) containing no test compound, was also sprayed on plants. A treated control with a commercial technical compound, chlorpyrifos or cypermethrin, formulated in the same manner, was tested as a standard. When dry, pots, to which 20 randomly selected hoppers (mostly nymphal stage were added) were place in a greenhouse at 26° C. The pots were then covered with ventilated propagator tops (wire gauze top closures) and held for 4–5 days after which the hoppers were examined for percent mortality.

Southern armyworm on tomato-systemic evaluation: This test was conducted in conjunction with the southern root-knot nematode evaluation (discussed below). The tomato plants, grown in the soil (at an initial compound test screening rate of 13.2 ppm soil concentration or about 333 ppm solution concentration) for nematode evaluation, were then utilized for evaluation of a compound's uptake via roots and subsequent systemic transport to the tomato foliage. At the termination of the nematode test, the tomato foliage was excised, placed into a plastic container, and infested with second instar larvae of southern armyworm. After about 5 days, the larvae were examined for percent mortality.

Southern armyworm (on Sorghum and cotton), cotton aphid (on cotton), and greenbug (on sorghum)-systemic evaluation: The stock solution of the compound was prepared as in the above systemic tests and diluted, as appropriate, to deliver 5 ml of a 10 ppm soil concentration dose as a drench (150 ppm solution concentration) to 6 cm pots containing cotton and sorghum plants. The cotton plants were previously infested with cotton aphids about 2 day before treatment and with greenbug one day before treatment. After holding the plants about 4 days, the cotton aphids and greenbugs were counted and mortality was assessed. The cotton and sorghum foliage was excised, and placed in separate plastic containers, and infested with second instar larvae of southern armyworm. After about 5 days, the larvae were examined for percent mortality.

Mexican bean beetle: Potted bean plants were placed on a revolving turntable and sprayed with 100 ml of the 100 ppm test compound formulation, sufficient to wet the plants to runoff, by use of a DeVilbiss spray gun set at 40 psig air pressure. As an untreated control, 100 ml of a water-acetone-DMF-emulsifier solution, containing no test compound, were also sprayed on plants. A treated control with a commercial technical compound, either cypermethrin or sulprofos, formulated in the same manner, was tested as a standard. When dry, the leaves were placed in plastic cups lined with moistened filter paper. Five randomly selected second instar Mexican bean beetle larvae were introduced into each cup which was closed and held for five days. Larvae which were unable to move the length of the body, even upon stimulation by prodding, were considered dead.

House fly: Four to six day old adult house flies were reared according to the specifications of the Chemical Specialties Manufacturing Association (Blue Book, McNair-Dorland Co., New York 1954; pages 243–244, 261) under controlled conditions. The flies were immobilized by anesthetizing with carbon dioxide and twenty five immobilized individuals, males and females, were transferred to a cage consisting of a standard food strainer and a wrapping-paper-covered surface. Ten ml of the 100 ppm test compound formulation were added to a soufflé cup containing an absorbent cotton pad. As an untreated control, 10 ml of a water-acetone-DMF-emulsifier-sucrose solution, containing no test compound, were applied in a similar manner. A treated control with a commercial technical compound, malathion, formulated in the same manner, was tested as a standard. The bait cup was introduced inside the food strainer prior to admitting the anesthetized flies. After 24 hours, flies which showed no sign of movement on stimulation were considered dead.

Southern corn rootworm: Into a jar containing 60 g of sandy loam soil was added 1.5 ml of an aqueous formulation consisting of an aliquot of the 200 ppm test compound formulation, diluted with water as appropriate for the final soil concentration of the test compound, 3.2 ml of water and five pregerminated corn seedlings. The jar was shaken thoroughly to obtain an even distribution of the test formulation. Following this, twenty southern corn rootworm eggs were placed into a cavity, which was made in the soil. Vermiculite(1 ml) and water (1.7 ml) were then added to this cavity. In a similar manner, an untreated control was prepared by application of the same size aliquot of a water-acetone-DMF-emulsifier solution, containing no test compound. Additionally, a treated control with a commercial technical compound (selected typically from terbufos, fonofos, phorate, chlorpyrifos, carbofuran, isazophos, or ethoprop), formulated in the same manner was used as needed as a test standard. After 7 days, the living rootworm larvae were counted using a well known "Berlese" funnel extraction method.

Southern root-knot nematode: Infected roots of tomato plants, containing egg masses of southern root-knot nematode, were removed from a stock culture and cleaned of soil by shaking and washing with tap water. The nematode eggs were separated from the root tissue and rinsed with water. Samples of the egg suspension were placed on a fine screen over a receiving bowl, in which the water level was adjusted to be in contact with the screen. From the bowl, juveniles were collected on a fine screen. The bottom of a cone-shaped container was plugged with coarse vermiculite and then filled to within 1.5 cm of the top with about a 200 ml volume of pasteurized soil. Then into a hole made in the center of the soil in the cone was pipetted an aliquot of the 333 ppm test compound formulation. A treated control with a commercial technical compound, fenamifos, formulated in a similar manner, was tested as a standard. As an untreated control, an aliquot of a water-acetone-DMF-emulsifier solution, containing no test compound, was applied in a similar manner. Immediately after treatment of the soil with the test compound there were added to the top of each cone 1000 second stage juvenile southern root-knot nematodes. After 3 days, a single healthy tomato seedling was then transplanted into the cone. The cone, containing the infested soil and tomato seedling, was kept in the greenhouse for 3 weeks. At the termination of the test, roots of the tomato seedling were removed from the cone and evaluated for galling on a rating scale relative to the untreated control as follows:

1-severe galling, equal to untreated control
3-light galling
4-very light galling
5-no galling, i.e., complete control These results were then converted to an $ED_3$ or $ED_5$ value (effective dose to provide a 3 or 5 gall rating).

Use Results: Results of miticidal, insecticidal, and nematicidal activity for some of the representative compound EXAMPLES 1-27 of the invention are discussed below or some compound EXAMPLES are set forth in TABLE 3 against the indicated test species (BA, SAW, MBB, HF, TSM, SCRW: designated by common name abbreviations) and at the indicated dosage rates. The results in TABLE 3 are presented (by an X) as compounds which provide a 70–100% mortality against the indicated test species. Compounds also control tobacco budworm, where for example, compounds of EXAMPLES 1, 5, 6, 8 and 9 provide 70–100% mortality as a bait application at 100 ppm.

Some of the compounds additionally exhibit systemic control of insect larvae and aphids via root uptake at the soil concentrations specified in the above protocols. The results are as follows: 30–100% control of southern armyworm on tomato (compounds of EXAMPLES 2, 3, 9, 10, 14, 18 and 22; 30–100% control of southern armyworm on sorghum (compounds of EXAMPLES 2, 9, and 21); 30–69% control of southern armyworm on cotton (compound of EXAMPLE 2); 30–100% control of cotton aphid on cotton (compounds of EXAMPLES 1, 9, 14, and 21); and 70–100% control of greenbug on sorghum (compounds of EXAMPLES 9, 10, 14, and 21).

Some compounds of the invention also provide control of certain grain pests where for example at test concentrations of about 5–10 ppm foliar concentration of the test compound, about 90 to 100% control of greenleaf hopper is obtained with compounds of EXAMPLES 2 and 10 and about 90 to 100% control of brown plant hopper is obtained with compounds of EXAMPLES 1, 2, 5, 10 and 18.

Nematicidal activity is additionally provided by compounds of the invention where, for example, compounds of EXAMPLES 22, 23 and 26, gave $ED_3$ values on SRKN of between about 4 to 21 kg/ha.

Furthermore, compounds of the invention exhibit reduced or antifeeding properties for some pest species, for example for foliar pests such as southern armyworm and Mexican bean beetle.

The compounds of the invention have utility against various pest species at even lower rates, for example: for foliar application, rates in the range of about 50–0.5 ppm, or less, may be useful; for bait application, rates in the range of about 50–0.5 ppm, or less, may be useful; and for soil application, rates in the range of about 1.0–0.01 ppm, or less, may be useful.

In the above discussion and the results reported in TABLE 3, compounds according to the invention are applied at various concentrations. The use of a 1 ppm (concentration of the compound in parts per million of the test solution applied) foliar solution or suspension or emulsion corresponds approximately to an application of 1 g/ha of active ingredient, based upon an approximate spray volume of 1000 liters/ha (sufficient to run off). Thus applications of foliar sprays of from about 6.25 to 500 ppm would correspond to about 6–500 g/ha. For soil applications, a 1 ppm soil concentration, on the basis of about a 7.5 cm soil depth, corresponds to an approximate 1000 g/ha broadcast field application. Or alternatively stated, a 1 ppm soil concentration as above, but as an approximate 18 cm band application corresponds to an approximate 166 g/ha.

TABLE 3

USE EXAMPLE OF PESTICIDAL ACTIVITY OF REPRESENTATIVE PYRIDYLPYRAZOLE COMPOUNDS PROVIDING 70–100% PEST MORTALITY

| CMPD. OF EXAMPLE | Foliar or Bait Application at 100 ppm | | | | | Soil conc. - .5 ppm |
|---|---|---|---|---|---|---|
| | BA | SAW | MBB | HF | TSM | SCRW |
| 1 | X | X | X | X | X | |
| 2 | X | X | X | X | X | |
| 3 | X | X | X | X | X | |
| 4 | | | | X | | |
| 5 | X | X | X | X | | |
| 6 | X | X | X | X | | X |
| 8 | X | X | X | X | X | |
| 9 | X | X | X | | X | |
| 10 | X | X | X | X | X | X |
| 11 | | | | X | | |
| 12 | | | | X | | |
| 13 | | | | X | | |
| 14 | X | X | X | X | | |
| 16 | | | | X | | |
| 17 | | | | X | | |
| 18 | X | X | X | X | X | X |
| 19 | | X | X | | | |
| 20 | X | | | X | | |
| 21 | X | X | | X | | X |
| 22 | X | | X | X | | |
| 23 | | | | X | | |
| 26 | X | | | X | | |

METHODS AND COMPOSITIONS

As is evident from the foregoing pesticidal uses, the present invention provides pesticidally active compounds and methods of use of said compounds for the control of a number of pest species which includes: arthropods, especially insects or mites; plant nematodes; or helminth or protozoan pests. The compounds thus are advantageously employed in practical uses, for example, in agricultural or horticultural crops, forestry, veterinary medicine or livestock husbandry, or in public health.

A feature of the present invention therefore provides a method of control of pests at a locus which comprises the treatment of the locus (e.g., by application or administration) with an effective amount of a compound of general formula (I) and more preferably a compound of formula (II), wherein the substituent groups are as hereinbefore defined. The locus includes, for example, the pest itself or the place (plant, animal, person, field, structure, premises, forest, orchard, waterway, soil, plant or animal product, or the like) where the pest resides or feeds.

The compounds of this invention are preferably used to control soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

Furthermore, these compounds may be useful in the control via foliar application or systemic action of some arthropods, especially some insects or mites, which feed on the above ground portions of plants. Control of foliar pests may additionally be provided by application to the plant roots or plant seeds with subsequent systemic translocation to the above ground portions of the plants.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

Compounds of the invention may be used in the following applications and on the following pests including arthropods, especially insects or mites, nematodes, or helminth or protozoan pests:

In the protection of stored products, for example cereals, including grain or flour, groundnuts, animal feedstuffs, timber or household goods, e.g. carpets and textiles, compounds of the invention are useful against attack by arthropods, more especially beetles, including weevils, moths or mites, for example *Ephestia* spp. (flour moths), *Anthrenus* spp. (carpet beetles), *Tribolium* spp. (flour beetles), *Sitophilus* spp. (grain weevils) or *Acarus* spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, *Reticulitermes* spp., *Heterotermes* spp., *Coptotermes* spp..

In agriculture against adults, larvae and eggs of Lepidoptera (butterflies and moths), e.g. *Heliothis* spp. such as *Heliothis virescens* (tobacco budworm), *Heliothis armigera* and *Heliothis zea*, Spodoptera spp. such as *S. exempta, S. frugiperda, S. exiqua, S. littoralis* (Egyptian cotton worm), *S. eridania* (southern army worm), and *Mamestra configurata* (bertha army worm); Earias spp. e.g. *E. insulana* (Egyptian bollworm), Pectinophora spp. e.g. *Pectinophora gossypiella* (pink bollworm), Ostrinia spp. such as *O. nubilalis* (European cornborer), *Trichoplusia ni* (cabbage looper), Artogeia spp. (cabbage worms), Laphygma spp. (army worms), Agrotis and Amathes spp. (cutworms), Wiseana spp. (porina moth), Chilo spp. (rice stem borer), Tryporyza spp. and Diatraea spp. (sugar cane borers and rice borers), Sparganothis pilleriana (grape berry moth), *Cydia pomonella* (codling moth), Archips spp. (fruit tree tortrix moth), *Plutella xylostella* (diamond back moth), *Bupalus piniarius, Cheimatobia brumata, Lithocolletis blancardella, Hyponomeuta padella, Plutella maculipennis, Malacosoma neustria, Euproctis chrysorrhoea*, Lymantria spp. *Bucculatrix thurberiella, Phyllocnistis citrella*, Euxoa spp., *Feltia brassicae, Panolis flammea, Prodenia litura, Carpocapsa pomonella, Pyrausta nubilalis, Ephestia kuehniella, Galleria mellonella, Tineola bisselliella, Tinea pellionella, Hofmannophila pseudospretella, Cacoecia podana, Capus reticulana, Choristoneura fumiferana, Clysia ambiguellis, Homona magnanime* and *Tortix viridana*.

Against adults and larvae of Coleoptera (beetles) e.g. *Hypothenemus hampei* (coffee berry borer), Hylesinus spp. (bark beetles), Anthonomus spp. e.g. grandis (cotton boll weevil), Acalymma spp. (cucumber beetles), Lema spp., Psylliodes spp., *Leptinotarsa decemlineata* (Colorado potato bettle), Diabrotica spp. (corn rootworms), Gonocephalum spp. (false wire worms), Agriotes spp., Limonius spp. (wireworms), Dermolepida spp., Popillia spp., Heteronychus spp. (white grubs), *Phaedon cochleariae* (mustard beetle), Epitrix spp. (flea beetles), *Lissorhoptrus oryzophilus* (rice water weevil), Meligethes spp. (pollen beetles), Ceutorhynchus spp., Rhynchophorus and Cosmopolites spp. (root weevils), *Anobium punctatum, Rhizopertha dominica, Bruchidius obtectus, Acanthoscelides obtectus, Hylotrupes bajulus, Agelastica alni, Psylliodes chrysocephala, Epilachna varivestis,* Atomaria spp., *Oryzaephilus surinamensis,* Sitophilus spp., *Otiorrhynchus sulcatus, Cosmoplites sordidus, Ceuthorrhynchus assimilis, Hypera postica,* Dermestes spp., Trogoderma spp., Anthrenus spp., Attagenus spp., Lyctus spp., *Maligethes aeneus,* Ptinus spp., *Niptus hololeucrus, Gibbium psylloides,* Tribolium spp., *Tenebrio molitor,* Conoderus spp., *Melolontha melolontha, Amphimallon solstitialis* and *Costelytra zealandica.*

Against Heteroptera (Hemiptera and Homoptera) e.g. Psylla spp., Bemisia spp., Trialeurodes spp., Aphis spp., Myzus spp., *Megoura viciae,* Phylloxera spp., Adelges spp., *Phorodon humuli* (hop damson aphid), Aeneolamia spp., Nephotettix spp. (rice leaf hoppers), Empoasca spp., Nilaparvata spp., Perkinsiella spp., Pyrilla spp., Aonidiella spp. (red scales), Coccus spp., Pseucoccus spp., Helopeltis spp. (mosquito bugs), Lygus spp., Dysdercus spp., Oxycarenus spp., Nezara spp., Eurygaster spp., *Piesma quadrata, Cimex lectularius, Rhodnius prolixus* and Triatoma spp. *Aspidiotus hederae, Aeurodes brassicae, Brevicoryne brassicae, Cryptomyzus ribis, Doralis fabae, Doralis pomi., Eriosoma lanigerum, Hyalopterus arundinis, Macrosiphum avenae, Phorodon humuli, Rhopalosiphum padi, Euscelis bilobatus, Nephotettix cincticeps, Lecanium corni, Saissetia oleae, Laodelphax striatellus.*

Against Hymenoptera e.g. Athalia spp. and Cephus spp. (saw flies), Atta spp. (leaf cutting ants), Diprion spp., Hopolocampa spp., Lasius spp., Monomorium spp., Polistes spp., Vespa spp., Vespula spp., and Solenopsis spp.

Against Diptera e.g. Delia spp. (root maggots), Atherigona spp. and Chlorops spp., Sarcophaga spp., Musca spp, Phormia spp., Aedes spp., Anopheles spp., Simulium spp., (shoot flies), Phytomyza spp. (leaf miners), Ceratitis spp. (fruit flies), Culex spp., *Drosophila melanogaster, Ceratitis capitata, Dacus oleae, Tipula paludosa, Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Fannia spp., *Bibio hortulanus, Oscinella frit,* Phorbia spp., *Pegomyia hyoscyani.*

Against Thysanoptera such as *Thrips tabaci, Hercinothrips femoralis,* and Frankliniella spp.

Against Orthoptera such as Locusta and Schistocerca spp., (locusts and crickets) e.g. Gryllus spp., and Acheta spp. for example, *Blatta orientalis, Periplaneta americana, Leucophaea maderae, Blatella germanica, Acheta domesticus,* Gryllotalpa spp., *Locusta migratoria migratorioides, Melanoplus differentialis* and *Schistocerca gregaria.*

Against Collembola e.g. Sminthurus spp. and Onychiurus spp. (springtails); Periplaneta spp. and Blattela spp. (roaches).

Against Isoptera e.g. Odontotermes spp., Reticuletermes spp., Coptotermes spp. (termites).

Against Dermaptera e.g. Forticula sp. (earwigs).

Against arthropods of agricultural significance such as Acari (mites) e.g. Tetranychus spp., Panonychus spp., Bryobia spp. (spider mites), Ornithonyssus spp. (fowl mites), Eriophyes spp. (gall mites), and Polyphadotarsonemus spp.

Against Thysanura, for example *Lepisma saccharia.*

Against Anoplura for example, *Phylloxera vastatrix,* Pemphigus spp., *Pediculus humanus corporis,* Haematopinus spp. and Linognathus spp.

Against Mallophaga, for example, Trichodectes spp. and Damalinea spp.

Against Siphonoptera, for example, *Xenopsylla cheopis* and Ceratophyllus spp.

Against other arthropods, such as Blaniulus spp. (millipedes), Scutigerella spp. (symphilids), Oniscus spp. (woodlice) and Triops spp. (crustacea).

Against Isopoda, for example, *Oniseus asellus, Armadillidium vulgare* and *Porcellio scaber.*

Against Chilopoda, for example, *Geophilus carpophagus* and *Scutigera spex.*

Against nematodes which attack plants or trees of importance to agriculture, forestry or horticulture either directly or by spreading bacterial, viral, mycoplasma or fungal diseases of the plants. For example root-knot nematodes such as Meloidogyne spp. (e.g. *M. incognita*); cyst nematodes such as Globodera spp. (e.g. *G. rostochiensis*); Heterodera spp. (e.g. *H. avenae*); Radopholus spp. (e.g. *R. similis*; lesion nematodes such as Pratylenchus spp. (e.g. *P. pratensis*); Belonolaimus spp. (e.g. *B. gracilis*); Tylenchulus spp. (e.g. *T. semipenetrans*); Rotylenchulus spp. (e.g. *R. reniformis*); Rotylenchus spp. (*R. robustus*); Helicotylenchus spp. (e.g. *H. multicinctus*); Hemicycliophora spp. (e.g. *H. gracilis*); Criconemoides spp. (e.g. *C. similis*); Trichodorus spp. (e.g. *T. primitivus*); dagger nematodes such as Xiphinema spp. (e.g. *X. diversicaudatum*), Longidorus spp. (e.g. *L. elongatus*); Hoplolaimus spp. (e.g. *H. coronatus*); Aphelenchoides spp. (e.g. *A. ritzema-bosi, A. besseyi*); stem and bulb eelworm such as Ditylenchus spp. (e.g. *D. dipsaci*).

In the field of veterinary medicine or livestock husbandry or in the maintenance of public health against arthropods, helminths or protozoa which are parasitic internally or externally upon vertebrates, particularly warm-blooded vertebrates, for example man or domestic animals, e.g. cattle, sheep, goats, equines, swine, poultry, dogs or cats, for example Acarina, including ticks (e.g. Ixodes spp., Boophilus spp. e.g. *Boophilus microplus,* Amblyomma spp., Hyalomma spp., Rhipicephalus spp. e.g. *Rhipicephalus appendiculatus,* Haemaphysalis spp., Dermacentor spp., Ornithodorus spp. (e.g. *Ornithodorus moubata*) and mites (e.g. Damalinia spp., *Dermahyssus gallinae,* Sarcoptes spp. e.g. *Sarcoptes scabiei,* Psoroptes spp., Chorioptes spp;, Demodex spp., Eutrombicula spp.,); Diptera (e.g. Aedes spp., Anopheles spp., Musca spp., Hypoderma spp., Gasterophilus spp., Simulium spp); Hemiptera (e.g. Triatoma spp); Phthirapter (e.g. Damalinia spp., Linognathus spp.); Siphonaptera (e.g. Ctenocephalides spp., Dictyoptera (e.g. Periplaneta spp., Blatella spp.); Hymenoptera (e.g. *Monomorium pharaonis*); for example against infections of the gastro-intestinal tract caused by parasitic nematode worms, for example members of the family Tritochostrongylidae, *Nippostrongylus brasiliensis, Trichinella spiralis, Haemonchus contortus, Trichostrongylus colubri-*

*formis, Nematodirus batus, Ostertagis circumcincta, Trichostrongylus axei,* Cooperia spp. and *Hymenolepis nana*; in the control and treatment of protozoal diseases caused by, for example, Eimeria spp. e.g. *Eimeria tenella, Eimeria acervulina, Eimeria brunetti, Eimeria maxima* and *Eimeria necatrix, Trypanosoms cruzi,* Leishaminia spp., Plasmodium spp., Babesis spp., Trichomonadidae spp., Histomanas spp., Giardia spp., Toxoplasma spp., *Entamoeba histolytica* and Theileria spp.

The invention, as previously described, provides methods of control of pests via application or administration of an effective amount of compounds of formula (I) or (II) at a locus which comprises treatment of the locus.

In practical use for the control of arthropods, especially insects or mites, or nematode pests of plants, a method, for example, comprises applying to the plants or to the medium in which they grow an effective amount of a compound of the invention. For such a method, the active compound is generally applied to the locus in which the arthropod or nematode infestation is to be controlled at an effective rate in the range of about 0.005 kg to about 15 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. More preferably an effective rate range of the active compound is from about 0.01 kg/ha to about 2 kg/ha.

When a pest is soil-borne, the active compound generally in a formulated composition, is distributed evenly over the area to be treated (i.e., for example broadcast or band treatment) in any convenient manner. Application may be made, if desired, to the field or crop-growing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting. Additionally, a method of control may also comprise treatment of the seed prior to planting with subsequent control effected after planting the seed.

Methods of control of pests also consist of application to or treatment of the foliage of plants to control arthropods, especially insects or mites, or nematodes attacking the aerial parts of the plants. In addition, methods of control of pests by the invention compounds are provided to control pests which feed on parts of the plant remote from the point of application, e.g., leaf feeding insects which are controlled via systemic action of the active compound when applied for example to the roots of a plant or to the plant seed prior to planting. Furthermore, the compounds of the invention may reduce attacks on a plant by means of antifeeding or repellent effects.

The compounds of the invention and methods of control of pests therewith are of particular value in the protection of field, forage, plantation, glasshouse, orchard or vineyard crops, of ornamentals, or of plantation or forest trees, for example: cereals (such as maize, wheat, rice, or sorghum), cotton, tobacco, vegetables (such as beans, cole crops, curcurbits, lettuce, onions, tomatoes or peppers), field crops (such as potatoes, sugar beets, ground nuts, soybeans, or oil seed rape), sugar cane, grassland or forage crops (such as maize, sorghum, or lucerne), plantations (such as tea, coffee, cocoa, banana, palm oil, coconut, rubber, or spices), orchards or groves (such as of stone or pit fruit, citrus, kiwifruit, avocado, mango, olives or walnuts), vineyards, ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compounds of the invention and methods of use thereof are of particular value in the control of arthropods, helminths or protozoa which are injurious to, or spread or act as vectors of diseases in man and domestic animals, for example those hereinbefore mentioned, and more especially in the control of ticks, mites, lice, fleas, midges, or biting, nuisance or myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

Furthermore, compounds of the invention may be useful for coccidiosis, a disease caused by infections from protozoan parasites of the genus Eimeria. It is an important potential cause of economic loss in domestic animals and birds, particularly those raised or kept under intensive conditions. For example, cattle, sheep, pigs or rabbits may be affected, but the disease is especially important in poultry, particularly in chickens. Administration of a small amount of a compound of the invention, preferably by a combination with feed is effective in preventing or greatly reducing the incidence of coccidiosis. The compounds are effective against both the cecal form and the intestinal forms. Furthermore, the compounds of the invention may also exert an inhibiting effect on oocytes by greatly reducing the number and sporulation of those produced. The poultry disease is generally spread by the birds picking up the infectious organism in droppings in or on contaminated litter, ground, food, or drinking water. The disease is manifested by hemorrhage, accumulation of blood in the ceca, passage of blood to the droppings, weakness and digestive disturbances. The disease often terminates in the death of the animal, but the fowl which survive severe infections have had their market value substantially reduced as a result of the infection.

The compositions hereinafter described for application to growing crops or crop growing loci or as a seed dressing may, in general, alternatively be employed for topical application to man or animals or in the protection of stored products, household goods, property or areas of the general environment. Suitable means of applying the compounds of the invention include:

to growing crops as foliar sprays, dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts;

to persons or animals infested by or exposed to infestation by arthropods, helminths or protozoa, by parenteral, oral or topical application of compositions in which the active ingredient exhibits an immediate and/or prolonged action over a period of time against the arthropods, helminths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;

to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water;

to domestic animals in feed to control fly larvae feeding in their feces;

In practice, the compounds of the invention most frequently form parts of compositions. These compositions can be employed to control: arthopods, especially insects or mites; nematodes; or helminth or protozoan pests. The compositions may be of any type known in the art suitable for application to the desired pest in any premises or indoor or outdoor area or by internal or external administration to vertebrates. These compositions contain at least one compound of the invention, such as described earlier, as the active ingredient in combination or association with one or more other compatible components which are for example, solid or liquid carriers or diluents, adjuvants, surface-active-agents, or the like appropriate for the intended use and which are agronomically or medicinally acceptable. These compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaridical use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Compositions, suitable for applications in agriculture, horticulture, or the like include formulations suitable for use as, for example, sprays, dusts, granules, fogs, foams, emulsions, or the like.

Compositions suitable for administration to vertebrates or man, include preparations suitable for oral, parenteral, percutaneous, e.g. pour-on, or topical administration.

Compositions for oral administration comprise one or more of the compounds of general formula(I) in association with pharmaceutically acceptable carriers or coatings and include, for example, tablets, pills, capsules, pastes, gels, drenches, medicated feeds, medicated drinking water, medicated dietary supplements, slow-release boluses or other slow-release devices intended to be retained within the gastro-intestinal tract. Any of these may incorporate the active ingredient contained within microcapsules or coated with acid-labile or alkali-labile or other pharmaceutically acceptable enteric coatings. Feed premixes or concentrates containing compounds of the present invention for use in preparation of medicated diets, drinking water or other materials for consumption by animals may also be used.

Compositions for parenteral administration include solutions, emulsions or suspensions in any suitable pharmaceutically acceptable vehicle or solid or semisolid subcutaneous implants or pellets designed to release the active ingredient over a protracted period of time and may be prepared and made sterile in any appropriate manner known to the art.

Compositions for percutaneous and topical administration include sprays, dusts, baths, dips, showers, jets, greases, shampoos, creams, wax-smears, or pour-on preparations or devices (e.g. ear tags attached externally to animals in such a way as to provide local or systemic arthropod control).

Solid or liquid baits, suitable for controlling arthropods, comprise one or more compounds of general formula(I) and a carrier or diluent which may include a food substance or some other substance to induce consumption by the arthropod.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminum or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or colouring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

Compositions containing compounds of general formula (I) which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate, e.g. benomyl and iprodione), bactericides, arthropod or vertebrate attractants or repellents or pheromones, deodorants, flavouring agents, dyes, or auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with the compositions of the present invention are: acephate, chlorpyrifos, demeton-S-methyl, disulfoton, ethoprofos, fenitrothion, fenamiphos, fonofos, isazophos, isofenphos, malathion, monocrotophos, paration, phorate, phosalone, pirimiphosmethyl, terbufos, triazophos, cyfluthrin, cypermethrin, deltamethrin, fenpropathrin, fenvalerate, permethrin, tefluthrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

For their agricultural application, the compounds of the formula(I) are therefore generally in the form of compositions, which are in various solid or liquid forms.

Solid forms of compositions which can be used are dusting powders (with a content of the compound of formula(I) ranging up to 80%), wettable powders or granules (including water dispersible granules), particularly those obtained by extrusion, compacting, impregnation of a granular carrier, or granulation starting from a powder (the content of the compound of formula(I) in these wettable powders or granules being between about 0.5 and about 80%). Solid homogenous or heterogenous compositions containing one or more compounds of general formula(I) for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (e.g. low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 20% by weight, or with an aqueous solution of a dispersing agent or binder, followed by drying and screening), or by a dry route (compacting followed by grinding and screening).

The application dose (effective dose) of active ingredient, also as a formulated composition, is generally between about 0.005 and about 15 kg/ha, preferably between about 0.01 and about 2 kg/ha. Therefore, the rates and concentrations of the formulated compositions may vary according to the method of application or the nature of the compositions or use thereof. Generally speaking, the compositions for application to control arthropod, plant nematode, helminth or protozoan pests usually contain from about 0.00001% to about 95%, more particularly from about 0.0005% to about 50% by weight of one or more compounds of general formula(I) or of total active ingredients (that is to say the compound(s) of general formula(I) together with: other substances toxic to arthropods or plant nematodes, anthelmintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of general formula(I). For administration to animals orally or parenterally, including percutaneously solid or liquid compositions, these normally contain from about 0.1% to about 90% by weight of one or more compounds of general formula(I). Medicated feedstuffs normally contain from about 0.001% to about 3% by weight of one or more compounds of general formula(I). Concentrates or supplements for mixing with feedstuffs normally contain from about 5% to about 90%, preferably from about 5% to about 50%, by weight of one or more compounds of general formula(I). Mineral salt licks normally contain from about 0.1% to about 10% by weight of one or more compounds of general formula(I).

Dusts or liquid compositions for application to livestock, persons, goods, premises or outdoor areas may contain from about 0.0001% to about 15%, more especially from about 0.005% to about 2.0%, by weight, of one or more compounds of general formula(I). Suitable concentrations in treated waters are between about 0.0001 ppm and about 20 ppm, more particularly about 0.001 ppm to about 5.0 ppm. of one or more compounds of general formula(I) and may be used therapeutically in fish farming with appropriate exposure times. Edible baits may contain from about 0.01% to about 5%, preferably from about 0.01% to about 1.0%, by weight, of one or more compounds of general formula(I).

When administered to vertebrates parenterally, orally or by percutaneous or other means, the dosage of compounds of general formula(I) will depend upon the species, age, or health of the vertebrate and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition EXAMPLES 29A-29L illustrate compositions for use against arthropods, especially mites or insects, plant nematodes, or helminth or protozoan pests which comprises, as active ingredient, compounds of general formula (I), especially compounds according to formula (II), such as those described in preparative EXAMPLES 1 to 27. The compositions described in EXAMPLES 29A-29F can each be diluted in water to give a sprayable composition at concentrations suitable for use in the field. Generic chemical descriptions of the ingredients (for which all of the following percentages are in weight percent), used in the composition EXAMPLES 29A-29L exemplified below, are as follows:

| Trade Name | Chemical Description |
|---|---|
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan No2 | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

EXAMPLE 29A

A water soluble concentrate is prepared with the composition as follows:

| Active ingredient | 7% |
|---|---|
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

EXAMPLE 29B

An emulsifiable concentrate (EC) is prepared with the composition as follows:

| Active ingredient | 7% |
|---|---|
| Soprophor BSU | 4% |
| Arylan CA | 4% |
| N-methylpyrrolidone | 50% |
| Solvesso 150 | 35% |

The first three components are dissolved in N-methylpyrrolidone and to this is then added the Solvesso 150 to give the final volume.

EXAMPLE 29C

A wettable powder (WP) is prepared with the composition as follows:

| Active ingredient | 40% |
|---|---|
| Arylan S | 2% |
| Darvan No2 | 5% |
| Celite PF | 53% |

The ingredients are mixed and ground in a hammer-mill to a powder with a particle size of less than 50 microns.

EXAMPLE 29D

An aqueous-flowable formulation is prepared with the composition as follows:

| Active ingredeint | 40.00% |
|---|---|
| Ethylan BCP | 1.00% |
| Sopropon T360. | 0.20% |
| Ethylene glycol | 5.00% |
| Rhodigel 230. | 0.15% |
| Water | 53.65% |

The ingredients are intimately mixed and are ground in a bead mill until a mean particle size of less than 3 microns is obtained.

EXAMPLE 29E

An emulsifiable suspension concentrate is prepared with the composition as follows:

| Active ingredient | 30.0% |
|---|---|
| Ethylan BCP | 10.0% |
| Bentone 38 | 0.5% |
| Solvesso 150 | 59.5% |

The ingredients are intimately mixed and ground in a beadmill until a mean particle size of less than 3 microns is obtained.

EXAMPLE 29F

A water dispersible granule is prepared with the composition as follows:

| Active ingredient | 30% |
|---|---|
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

EXAMPLE 29G

A dusting powder is prepared with the composition as follows:

| Active ingredient | 1 to 10% |
|---|---|
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

EXAMPLE 29H

An edible bait is prepared with the composition as follows:

| Active ingredient | 0.1 to 1.0% |
|---|---|
| Wheat flour | 80% |

| | |
|---|---|
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

EXAMPLE 29I

A solution formulation is prepared with a composition as follows:

| | |
|---|---|
| Active ingredient | 15% |
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

EXAMPLE 29J

A wettable powder is prepared with the composition as follows:

| | |
|---|---|
| Active ingredient | 50% |
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, helminths or protozoa, by spraying or dipping, or by oral administration in drinking water, to control the arthropods, helminths or protozoa.

EXAMPLE 29K

A slow release bolus composition is formed from granules containing the following components in varying percentages (similar to those described for the previous compositions) depending upon need:
Active ingredient
Density agent
Slow-release agent
Binder The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods, helminths or protozoa.

EXAMPLE 29L

A slow release composition in the form of granules, pellets, brickettes or the like can be prepared with compositions as follows:

| | |
|---|---|
| Active ingredient | 0.5 to 25% |
| Polyvinyl chloride | 75 to 99.5% |
| Dioctyl phthalate (plasticizer) | catalytic amount |

The components are blended and then formed into suitable shapes by melt-extrusion or molding. These composition are useful, for example, for addition to standing water or for fabrication into collars or eartags for attachment to domestic animals to control pests by slow release.

While the present invention has been set forth in specific and illustrative details and described with preferred particularity, it is susceptible to changes, modifications or alternations, obvious to one of ordinary skill in the art, without departing from the scope and spirit of the invention, which is defined by the claims appended hereto.

What we claim is:

1. A compound of formula (I),

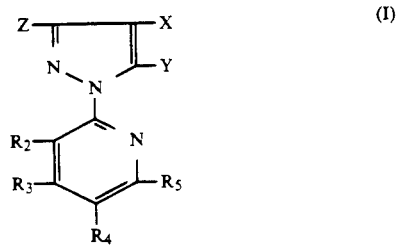

wherein:
X is halogen, nitro, or unsubstituted or halo-substituted alkylsulfenyl, alkylsulfinyl or alkylsulfonyl, wherein the alkyl moiety is a linear or branched chain, containing one to four carbon atoms, and the halo-substitution consists of one or more halogen atoms, which are the same or different, up to full substitution of the alkyl moiety;

Y is hydrogen, halogen, cyano, alkylsulfenyl, alkylsulfinyl, alkylsulfonyl, amino, alkylamino, dialkylamino, trialkylammonium salt, cyanoalkylamino, alkoxyalkylamino, alkoxycarbonylamino, alkylcarbonylamino, haloalkylcarbonylamino, alkylaminocarbonylamino, dialkylaminocarbonylamino or alkoxyalkylideneimino, wherein the alkyl and alkoxy moieties are a linear or branched chain, containing one to four carbon atoms, and the halo-substitution consists of one or more halogen atoms, which are the same or different, up to full substitution of the alkyl moiety;

Z is cyano or halogen; and $R_2$, $R_3$, $R_4$, and $R_5$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that at least one of $R_2$ to $R_5$ is other than hydrogen.

2. The compound of claim 1 of formula (I), wherein X is $S(O)_nR_1$, having a formula (II),

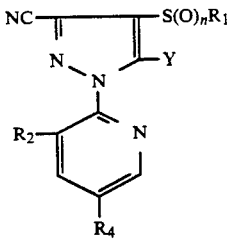

(II)

wherein:
Y is hydrogen, halogen, cyano, alkylsulfenyl, alkylsulfinyl, alkylsulfonyl, amino, alkylamino, dialkylamino, trialkylammonium salt, cyanoalkylamino, alkoxyalkylamino, alkoxycarbonylamino, alkylcarbonylamino, haloalkylcarbonylamino, alkylaminocarbonylamino, dialkylaminocarbonylamino or alkoxyalkylideneimino, wherein the alkyl and alkoxy moieties are a linear or branched chain, containing one to four carbon atoms, and the halo-substitution consists of one or more halogen atoms, which are the same or different, up to full substitution of the alkyl moiety;

$R_1$ is a linear or branched alkyl of one to four carbon atoms, which is substituted by one or more halogen atoms, which are the same or different, up to full substitution of the alkyl group;

n is 0, 1 or 2; and $R_2$ and $R_4$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that one of $R_2$ and $R_4$ is other than hydrogen.

3. The compound of claim 2 of formula (II), having a formula (IIa), wherein:

Y is amino, alkylamino, alkylsulfenyl, alkylsulfinyl, alkylsulfonyl, alkoxyalkylamino, alkylcarbonylamino, haloalkylcarbonylamino or alkoxyalkylideneimino, wherein the alkyl and alkoxy moieties are a linear or branched chain, containing one to four carbon atoms, and the halo-substitution consists of one or more halogen atoms, which are the same or different, up to full substitution of the alkyl moiety;

$R_2$ is hydrogen or halogen;

$R_4$ is hydrogen, halogen, haloalkyl or haloalkoxy, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that one of $R_2$ and $R_4$ is other than hydrogen.

4. The compound of claim 3 of formula (IIa), having a formula (IIb), wherein:

Y is amino, alkylamino, alkoxymethylamino or alkoxyalkylideneimino, wherein the alkyl and alkoxy moieties contain one or two carbon atoms;

$R_1$ is trifluoromethyl, dichlorofluoromethyl or chlorodifluoromethyl;

$R_2$ is bromine, chlorine or fluorine; and $R_4$ is bromine, chlorine, fluorine, trifluoromethyl or trifluoromethoxy.

5. The compound of claim 4, having a formula (IIb), which is:

1-[2-(3-chloro-5-trifluoromethyl)pyridyl]-5-amino-3-cyano-4-chlorodifluoromethylsulfenylpyrazole;

1-[2-(3-chloro-5-trifluoromethyl)pyridyl]-5-amino-3-cyano-4-chlorodifluoromethylsulfinylpyrazole;

1-[2-(3-chloro-5-trifluoromethyl)pyridyl]-5-amino-3-cyano-4-chlorodifluoromethylsulfonylpyrazole;

1-[2-(3-chloro-5-trifluoromethyl)pyridyl]-5-amino-3-cyano-4-dichlorofluoromethylsulfenylpyrazole;

1-[2-(3-chloro-5-trifluoromethyl)pyridyl]-5-ethoxymethylamino-3-cyano-4-dichlorofluoromethylsulfenylpyrazole;

1-[2-(3-chloro-5-trifluoromethyl)pyridyl]-5-amino-3-cyano-4-trifluoromethylsulfenylpyrazole;

1-[2-(3-chloro-5-trifluoromethyl)pyridyl]-5-amino-3-cyano-4-trifluoromethylsulfinylpyrazole;

1-[2-(3-chloro-5-trifluoromethyl)pyridyl]-5-amino-3-cyano-4-trifluoromethylsulfonylpyrazole;

1-[2-(3-chloro-5-trifluoromethyl)pyridyl]-5-amino-3-cyano-4-difluoromethylsulfinylpyrazole;

1-[2-(3-chloro-5-trifluoromethyl)pyridyl]-5-amino-3-cyano-4-dichlorofluoromethylsulfonylpyrazole;

1-[2-(3-chloro-5-trifluoromethyl)pyridyl]-5-amino-3-cyano-4-methylsulfenylpyrazole;

1-[2-(3-chloro-5-trifluoromethyl)pyridyl]-5-amino-3-cyano-4-methylsulfinylpyrazole; or 1-[2-(3,5-dichloro)pyridyl]-5-amino-3-cyano-4-trifluoromethylsulfenylpyrazole.

6. A compound of formula (III),

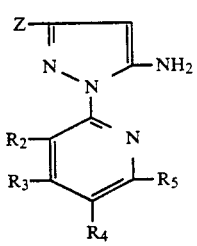

(III)

wherein:
Z is $C_{1-4}$ alkoxycarbonyl, aminocarbonyl or cyano; and $R_2$, $R_3$, $R_4$, and $R_5$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that at least one of $R_2$ to $R_5$ is other than hydrogen.

7. A compound of formula (IV),

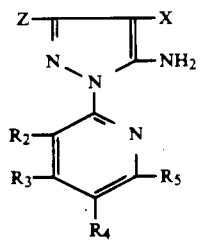

wherein:
Z is C$_{1-4}$ alkoxycarbonyl or aminocarbonyl;
X is halogen, nitro, or unsubstituted or halo-substituted alkylsulfenyl, alkylsulfinyl or alkylsulfonyl, wherein the alkyl moiety is a linear or branched chain, containing one to four carbon atoms, and the halo-substitution consists of one or more halogen atoms, which are the same or different, up to full substitution of the alkyl moiety; and
R$_2$, R$_3$, R$_4$, and R$_5$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that at least one of R$_2$ to R$_5$ is other than hydrogen.

8. A compound of formula (V), 21, 25, or 22,

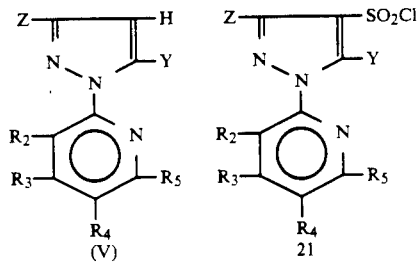

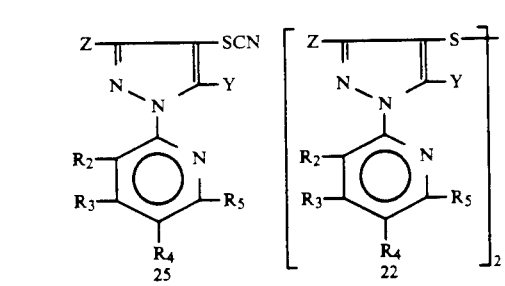

wherein:
Y is hydrogen, halogen, cyano, alkylsulfenyl, alkylsulfinyl, alkylsulfonyl, amino, alkylamino, dialkylamino, trialkylammonium salt, cyanoalkylamino, alkoxyalkylamino, alkoxycarbonylamino, alkylcarbonylamino, haloalkylcarbonylamino, alkylaminocarbonylamino, dialkylaminocarbonylamino or alkoxyalkylideneimino, wherein the alkyl and alkoxy moieties are a linear or branched chain, containing one to four carbon atoms, and the halo-substitution consists of one or more halogen atoms, which are the same or different, up to full substitution of the alkyl moiety;
Z is cyano or halogen; and
R$_2$, R$_3$, R$_4$, and R$_5$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that at least one of R$_2$ to R$_5$ is other than hydrogen.

9. The compound of any one of claims 6, 7 or 8 wherein:
Y is amino, alkylamino, alkoxymethylamino or alkoxyalkylideneimino, wherein the alkyl and alkoxy moieties contain one or two carbon atoms;
R$_2$ is bromine, chlorine or fluorine;
R$_3$ and R$_5$ are each hydrogen; and
R$_4$ is bromine, chlorine, fluorine, trifluoromethyl or trifluoromethoxy.

10. A method for the control of: arthropods; nematodes; or helminth or protozoan pests at a locus which comprises treatment of the locus with an effective amount of a compound of formula (I),

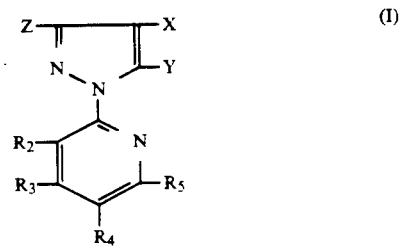

wherein:
X is halogen, nitro, or unsubstituted or halo-substituted alkylsulfenyl, alkylsulfinyl or alkylsulfonyl, wherein the alkyl moiety is a linear or branched chain, containing one to four carbon atoms, and the halo-substitution consists of one or more halogen atoms, which are the same or different, up to full substitution of the alkyl moiety;
Y is hydrogen, halogen, cyano, alkylsulfenyl, alkylsulfinyl, alkylsulfonyl, amino, alkylamino, dialkylamino, trialkylammonium salt, cyanoalkylamino, alkoxyalkylamino, alkoxycarbonylamino, alkylcarbonylamino, haloalkylcarbonylamino, alkylaminocarbonylamino, dialkylaminocarbonylamino or alkoxyalkylideneimino, wherein the alkyl and alkoxy moieties are a linear or branched chain, containing one to four carbon atoms, and the halo-substitution consists of one or more halogen atoms, which are the same or different, up to full substitution of the alkyl moiety;
Z is cyano or halogen; and
R$_2$, R$_3$, R$_4$, and R$_5$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that at least one of R$_2$ to R$_5$ is other than hydrogen.

11. The method of claim 10 of the compound of formula (I), having a formula (IIb),

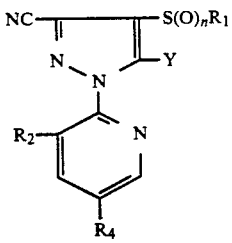

(IIb)

Y is amino, alkylamino, alkoxymethylamino or alkoxyalkylideneimino, wherein the alkyl and alkoxy moieties contain one or two carbon atoms;

$R_1$ is trifluoromethyl, dichlorofluoromethyl or chlorodifluoromethyl;

n is 0, 1 or 2;

$R_2$ is bromine, chlorine or fluorine; and $R_4$ is bromine, chlorine, fluorine, trifluoromethyl or trifluoromethoxy.

12. The method of claim 11, wherein the compound of formula (IIb) is:

1-[2-(3-chloro-5-trifluoromethyl)pyridyl]-5-amino-3-cyano-4-chlorodifluoromethylsulfenylpyrazole;

1-[2-(3-chloro-5-trifluoromethyl)pyridyl]-5-amino-3-cyano-4-chlorodifluoromethylsulfinylpyrazole;

1-[2-(3-chloro-5-trifluoromethyl)pyridyl]-5-amino-3-cyano-4-chlorodifluoromethylsulfonylpyrazole;

1-[2-(3-chloro-5-trifluoromethyl)pyridyl]-5-amino-3-cyano-4-dichlorofluoromethylsulfenylpyrazole;

1-[2-(3-chloro-5-trifluoromethyl)pyridyl]-5-ethoxymethylamino-3-cyano-4-dichlorofluoromethylsulfenylpyrazole;

1-[2-(3-chloro-5-trifluoromethyl)pyridyl]-5-amino-3-cyano-4-trifluoromethylsulfenylpyrazole;

1-[2-(3-chloro-5-trifluoromethyl)pyridyl]-5-amino-3-cyano-4-trifluoromethylsulfinylpyrazole;

1-[2-(3-chloro-5-trifluoromethyl)pyridyl]-5-amino-3-cyano-4-trifluoromethylsulfonylpyrazole;

1-[2-(3-chloro-5-trifluoromethyl)pyridyl]-5-amino-3-cyano-4-difluoromethylsulfinylpyrazole;

1-[2-(3-chloro-5-trifluoromethyl)pyridyl]-5-amino-3-cyano-4-dichlorofluoromethylsulfonylpyrazole;

1-[2-(3-chloro-5-trifluoromethyl)pyridyl]-5-amino-3-cyano-4-methylsulfenylpyrazole;

1-[2-(3-chloro-5-trifluoromethyl)pyridyl]-5-amino-3-cyano-4-methylsulfinylpyrazole; or 1-[2-(3,5-dichloro)pyridyl]-5-amino-3-cyano-4-trifluoromethylsulfenylpyrazole.

13. The method of claim 10, wherein the locus comprises agricultural or horticultural plants or a medium in which the plants grow and the pests are arthropod or nematode pests of the plants, and the treatment is by applying to the plants or to the medium in which they grow an effective amount of the compound of formula (I).

14. The method of claim of 13, wherein the compound is applied to the locus, in which the arthropod or nematode pests are controlled, at a rate of about 0.005 kg to about 15 kg of compound per hectare of locus treated.

15. The method of claim 14, wherein the compound is applied to the locus at a rate of about 0.02 kg to about 2 kg of compound per hectare.

16. The method of claim 13, wherein said pests are mites, aphids, insects or plant nematodes or combinations thereof, which comprises incorporating the compound into soil in which the plants are planted or are to be planted, or applying the compound to the plant's seeds, to the plant's roots, or to the plant's foliage.

17. The method of claim 16, wherein: said insects are soil insects in the Coleoptera order, Lepidoptera order or Diptera order or foliar insects in the Lepidoptera order, Coleoptera order, Homoptera order or Thysanoptera order; said mites are in the subclass Acari; and said aphids are in the Homoptera order.

18. The method of claim 10, wherein said method is employed in the field of veterinary medicine or livestock husbandry or in the maintenance of public health against arthropods, helminths or protozoa which are parasitic internally or externally upon warm-blooded vertebrates.

19. The method of claim 18, wherein said arthropods are insects in the Diptera order or mites in the subclass Acari or both.

20. A composition for the control of arthropod, nematode, helminth, or protozoan pests comprising; an agronomically acceptable carrier and an effective amount of a compound of formula (I),

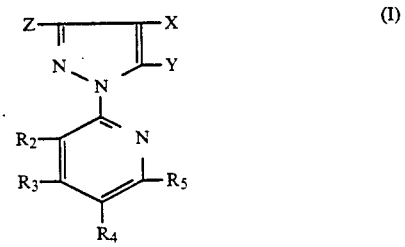

wherein:

X is halogen, nitro, or unsubstituted or halo-substituted alkylsulfenyl, alkylsulfinyl or alkylsulfonyl, wherein the alkyl moiety is a linear or branched chain, containing one to four carbon atoms, and the halo-substitution consists of one or more halogen atoms, which are the same or different, up to full substitution of the alkyl moiety;

Y is hydrogen, halogen, cyano, alkylsulfenyl, alkylsulfinyl, alkylsulfonyl, amino, alkylamino, dialkylamino, trialkylammonium salt, cyanoalkylamino, alkoxyalkylamino, alkoxycarbonylamino, alkylcarbonylamino, haloalkylcarbonylamino, alkylaminocarbonylamino, dialkylaminocarbonylamino or alkoxyalkylideneimino, wherein the alkyl and alkoxy moieties are a linear or branched chain, containing one to four carbon atoms, and the halosubstitution consists of one or more halogen atoms, which are the same or different, up to full substitution of the alkyl moiety;

Z is cyano or halogen; and $R_2$, $R_3$, $R_4$, and $R_5$ are each individually hydrogen, halogen, alkyl, haloalkyl, alkoxy, haloalkoxy, cyano or nitro, wherein the alkyl and alkoxy moieties are a linear or branched chain, containing one to four carbon atoms, and the halo-substitution consists of one or more halogen atoms, which are the same or different, up to full substitution of the alkyl and alkoxy moieties; and with the proviso that at least one of $R_2$ to $R_5$ is other than hydrogen.

21. The composition of claim 20, which contains 0.05 to 95% by weight of one or more compounds of formula (I) as active ingredient and 1 to 95% by weight of one or more agronomically or medicinally acceptable solid or liquid carriers.

22. The composition of claim 21, further comprising 0.5 to 50% by weight of one or more compatible components, which are agronomically or medicinally acceptable diluents, adjuvants or surface active-agents.

23. The composition of claim 20 wherein the compound of formula (I) has a formula (IIb),

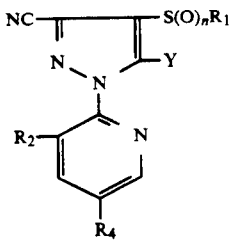
(IIb)

Y is amino, alkylamino, alkoxymethylamino or alkoxyalkylideneimino, wherein the alkyl and alkoxy moieties contain one or two carbon atoms;

$R_1$ is trifluoromethyl, dichlorofluoromethyl or chlorodifluoromethyl;

n is 0, 1 or 2;

$R_2$ is bromine, chlorine or fluorine; and $R_4$ is bromine, chlorine, fluorine, trifluoromethyl or trifluoromethoxy.

24. The composition of claim 23, wherein the compound of formula (IIb) is:

1-[2-(3-chloro-5-trifluoromethyl)pyridyl]-5-amino-3-cyano-4-chlorodifluoromethylsulfenylpyrazole;

1-[2-(3-chloro-5-trifluoromethyl)pyridyl]-5-amino-3-cyano-4-chlorodifluoromethylsulfinylpyrazole;

1-[2-(3-chloro-5-trifluoromethyl)pyridyl]-5-amino-3-cyano-4-chlorodifluoromethylsulfonylpyrazole;

1-[2-(3-chloro-5-trifluoromethyl)pyridyl]-5-amino-3-cyano-4-dichlorofluoromethylsulfenylpyrazole;

1-[2-(3-chloro-5-trifluoromethyl)pyridyl]-5-ethoxymethylamino-3-cyano-4-dichlorofluoromethylsulfenylpyrazole;

1-[2-(3-chloro-5-trifluoromethyl)pyridyl]-5-amino-3-cyano-4-trifluoromethylsulfenylpyrazole;

1-[2-(3-chloro-5-trifluoromethyl)pyridyl]-5-amino-3-cyano-4-trifluoromethylsulfinylpyrazole;

1-[2-(3-chloro-5-trifluoromethyl)pyridyl]-5-amino-3-cyano-4-trifluoromethylsulfonylpyrazole;

1-[2-(3-chloro-5-trifluoromethyl)pyridyl]-5-amino-3-cyano-4-difluoromethylsulfinylpyrazole;

1-[2-(3-chloro-5-trifluoromethyl)pyridyl]-5-amino-3-cyano-4-dichlorofluoromethylsulfonylpyrazole;

1-[2-(3-chloro-5-trifluoromethyl)pyridyl]-5-amino-3-cyano-4-methylsulfinylpyrazole;

1-[2-(3-chloro-5-trifluoromethyl)pyridyl]-5-amino-3-cyano-4-methylsulfinylpyrazole; or 1-[2-(3,5-dichloro)pyridyl]-5-amino-3-cyano-4-trifluoromethylsulfenylpyrazole.

* * * * *